(12) United States Patent
Davies et al.

(10) Patent No.: US 9,896,692 B2
(45) Date of Patent: *Feb. 20, 2018

(54) SUGARCANE BACILLIFORM VIRAL ENHANCER-BASED ACTIVATION TAGGING PLATFORM FOR MAIZE, AND RESULTANT TAGGED POPULATIONS AND PLANTS

(71) Applicant: Dow AgroSciences LLC, Indianapolis, IN (US)

(72) Inventors: John P. Davies, Portland, OR (US); Vaka S. Reddy, Aurora, CO (US); William Michael Ainley, Camel, IN (US); D. Ry Wagner, Pleasant Hill, OR (US); Xing Liang Liu, Lake Oswego, OR (US)

(73) Assignee: Dow AgroSciences LLC, Indianapolis, IN (US)

( * ) Notice: Subject to any disclaimer, the term of this patent is extended or adjusted under 35 U.S.C. 154(b) by 278 days.

This patent is subject to a terminal disclaimer.

(21) Appl. No.: 14/570,823

(22) Filed: Dec. 15, 2014

(65) Prior Publication Data
US 2015/0096080 A1 Apr. 2, 2015

Related U.S. Application Data

(63) Continuation of application No. 13/220,570, filed on Aug. 29, 2011, now Pat. No. 8,912,393.

(60) Provisional application No. 61/402,574, filed on Aug. 30, 2010.

(51) Int. Cl.
*C12N 15/82* (2006.01)
*C12Q 1/68* (2006.01)

(52) U.S. Cl.
CPC ..... *C12N 15/8209* (2013.01); *C12N 15/8205* (2013.01); *C12N 15/8241* (2013.01); *C12Q 1/6895* (2013.01); *C12Q 2600/13* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,013,658 A | 5/1991 | Dooner et al. | |
| 6,008,437 A | 12/1999 | Krebbers et al. | |
| 6,670,467 B2 * | 12/2003 | Barbour | C07K 14/415 435/252.3 |
| 7,169,967 B2 | 1/2007 | Streatfield et al. | |
| 7,250,553 B2 | 7/2007 | Liu et al. | |
| 2009/0093366 A1 | 4/2009 | Wright et al. | |

FOREIGN PATENT DOCUMENTS

| | | |
|---|---|---|
| WO | WO 1991/002059 | 2/1991 |
| WO | WO 00/12734 | 3/2000 |
| WO | WO 02/42450 A1 * | 5/2002 |

OTHER PUBLICATIONS

Tani et al., 2004, Funct. Integr. Genomics 4: 258-266.*
Al-Saady, 2002, PhD thesis, University of Minnesota, pp. 1-94.*
Bhat et al., 2016, Viruses 8, 177, doi:10.3390/v8060177.*
Memelink, 2003, In: Methods in Molecular Biology vol. 236: Plant Functional Genomics: Methods and Protocols, pp. 345-361.*
An et al., "Generation and Analysis of End Sequence Database for T-DNA Tagging Lines in Rice," *Plant Physiology*, 133: 2040-2047, 2005.
Ayliffe et al., "A barley activation tagging system," *Plant. Mol. Biol.*, 64(3): 329-347, 2007.
Braithwaite et al., "A variable region of the Sugarcane Bacilliform Virus (SCBV) genome can be used to generate promoter for transgene expression in sugarcane," *Plant Cell Rep*, 23: 319-326, 2004.
Brutnell, "Transposon tagging in maize," *Funct Integr Genomics*, 2: 4-12, 2002.
Chen et al., "Distribution and characterization of over 1000 T-DNA tags in rice genome," *The Plant Journal*, 36: 105-113, 2003.
Dong et al., "Novel Plant Activation-Tagging Vectors Designed to Minimize 35S Enhancer-Mediated Gene Silencing," *Plant Molecular Biology Reporter*, 21: 349-358, 2003.
Greco et al., "Transcription and somatic transposition of the maize En/Spm transposon system in rice," *Mol. Gen. Genomics*, 270(6): 514-523, 2004.
Jeong et al., "T-DNA Insertional Mutagenesis for Activation Tagging in Rice," *Plant Physiology*, 130(4): 1636-1644, 2002.
Komori et al., "Current Status of Binary Vectors and Superbinary Vectors," *Plant Physiology*, 130(4): 1636-1644, 2002.
Kuluev et al., "Activity of Promoters of Carnation Etched Ring Virus and Dahlia Mosaic Virus in Tobacco Protoplasts and Transgenic Plants," *Russian Journal of Plant Physiology*, 55(5): 687-693, 2008.
Kumar et al., "Efficient insertional mutagenesis in rice using the maize En/Spm elements," *The Plant Journal*, 44: 879-892, 2005.

(Continued)

*Primary Examiner* — Amjad Abraham
*Assistant Examiner* — Bratislav Stankovic
(74) *Attorney, Agent, or Firm* — Marcos P. Rivas; Barnes & Thornburg LLP

(57) ABSTRACT

An activation tagging construct for maize that includes one or more sugarcane bacilliform viral (SCBV) enhancer elements, and resulting tagged populations and plants, are described. In one example, an activation tagging DNA construct includes a coding sequence for a transposase, a detectable reporter (such as anthocyanin regulatory genes B-Peru and C1) and a non-autonomous transposable T-DNA cassette. For example, the transposable T-DNA cassette is inserted into the detectable reporter encoding region such that the B-Peru and C1 genes express anthocyanins in a cell containing the maize activation tagging DNA construct only upon excision of the transposable cassette. Methods of generating a tagged population of maize plants include transforming a maize plant cell or tissue with the disclosed constructs.

12 Claims, 5 Drawing Sheets
(5 of 5 Drawing Sheet(s) Filed in Color)

(56) References Cited

OTHER PUBLICATIONS

Marsh-Martinez et al., "Activation Tagging Using the En-I Maize Transposon System in *Arabidopsis*," *Plant Physiolog*, 129: 1544-1556, 2002.

Mathews et al., "Activation Tagging in Tomato Identifies a Transcriptional Regulator of Anthocyanin Biosynthesis, Modification, and Transport," *The Plant Cell*, 15: 1689-1703, 2003.

Menossi et al. "Improved Analysis of Promoter Activity in Biolistically Transformed Plant Cells," *BioTechniques*, 28(1): 54-58, 2000.

Meyers et al., "Abundance, Distribution, and Transcriptional Activity of Repetitive Elements in the Maize Genome," *Genome Res.*, 11: 1660-1676, 2001.

Qu et al., "A Versatile Transposon-Based Activation Tag Vector System for Functional Genomics in Cereals and Other Monocot Plants," *Plant Physiology*, 146:.189-199, 2008.

Sallaud et al., "High throughput T-DNA insertion mutagenesis in rice: a first step towards in silico reverse genetics," *The Plant Journal*, 39: 450-464, 2004.

Schneider et al., "A transposon-based activation-tagging population in *Arabidopsis thaliana* (TAMARA) and its application in the identification of dominant developmental and metabolic mutations," *FEBS Letters*, 579: 4622-4628, 2005.

Shen et al., "Pigmented maize seed via tissue-specific expression of anthocyanin pathway gene transcription factors," *Mol. Breeding*, 18: 57-67, 2006.

Speulman et al., "A Two-Component Enhancer-Inhibitor Transposon Mutagenesis System for Functional Analysis of the *Arabidopsis* Genome," *The Plant Cell*, 11: 1853-1866, 1999.

Tissier et al., "Multiple Independent Defective Suppressor-mutator Transposon Insertions in *Arabidopsis*: A Tool for Functional Genomics," *The Plant Cell*, 11: 1841-1852, 1999.

Vickers et al., "A novel cis-acting element, ESP, contributes to high-level endosperm-specific expression in an oat globulin promoter," *Plant Mol Biol*, 62: 195-214, 2006.

Weigel et al., "Activation Tagging in *Arabidopsis*," *Plant Physiology*, 122: 1003-1013, 2000.

Wendl and Barbazuk, "Extension of Lander-Waterman theory for sequencing filtered DNA libraries," *BMC Bioinformatics*, 6: 245-256, 2005.

Zuo et al., "The Wuschel gene promotes vegetative-to-embryonic transition in *Arabidopsis*," *The Plant Journal*, 30(3): 349-359, 2002.

* cited by examiner

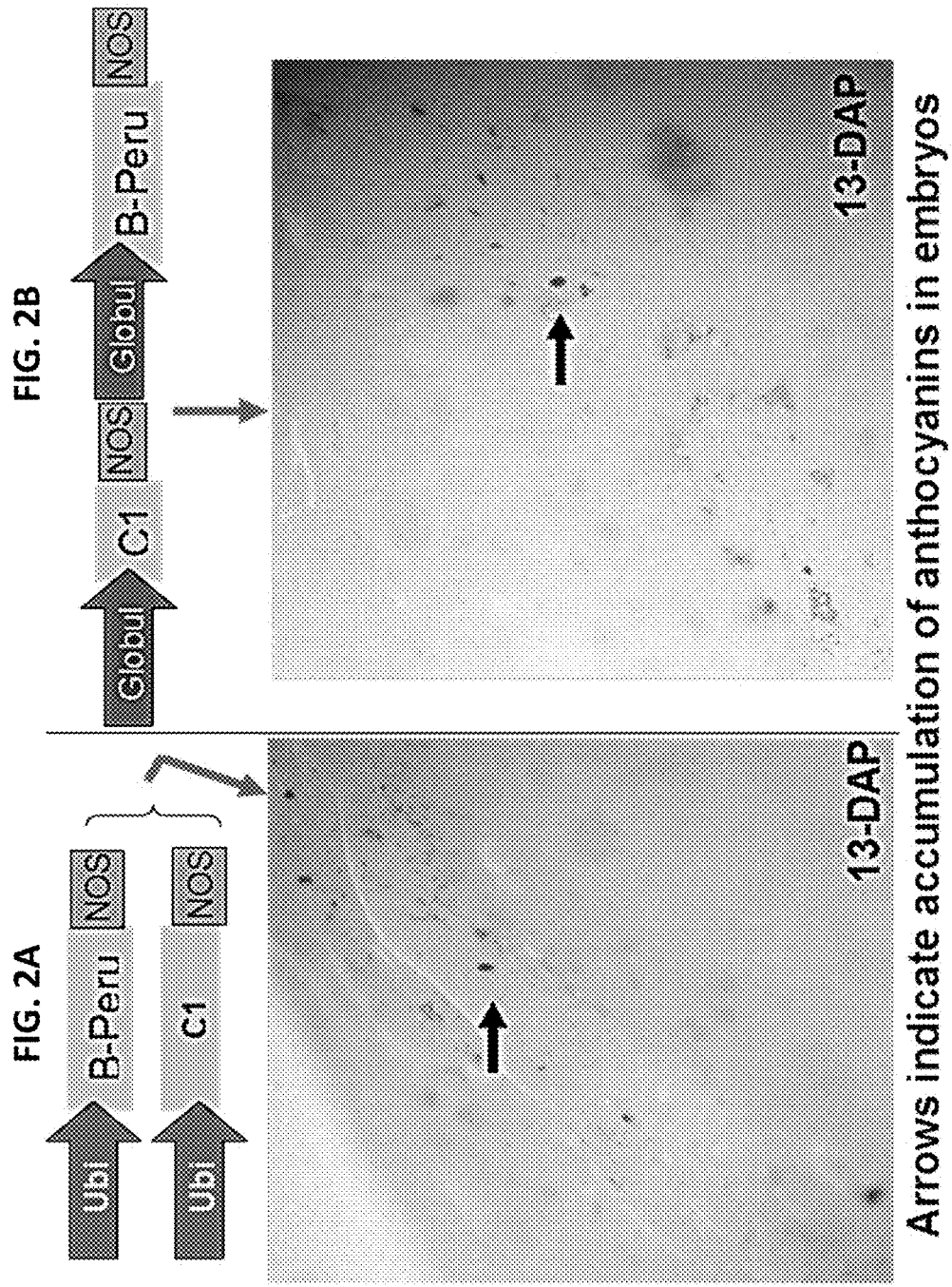

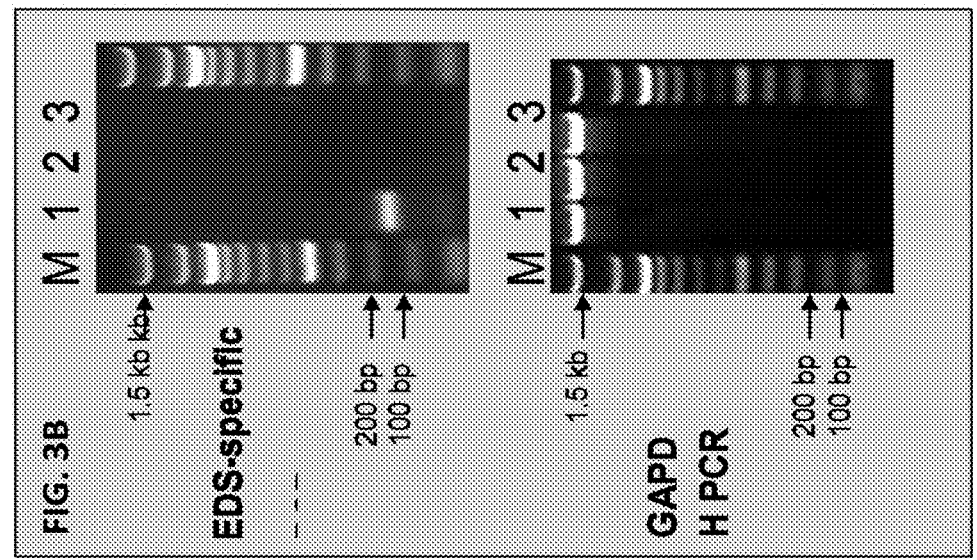
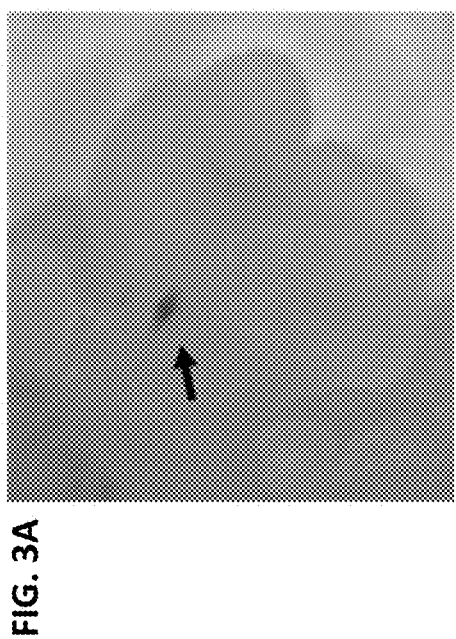
FIG. 3A
FIG. 3C Empty donor site (EDS)
```
EDS   :  cagtgt dSpm acgagaca
EDS 1 :: cagtgt      acgagaca
EDS 2 :: cagtgt   ..cgagaca
EDS 3 :: cagtgt   ..cgagaca
EDS 4 :: cagtgt   ..cgagac(t)
EDS 5 :: cag(c)gt ..cgagaca
EDS 6:  cagtg.    ...agaca
```

SUGARCANE BACILLIFORM VIRAL ENHANCER-BASED ACTIVATION TAGGING PLATFORM FOR MAIZE, AND RESULTANT TAGGED POPULATIONS AND PLANTS

PRIORITY CLAIM

The application submitted herewith is a continuation of co-pending U.S. application Ser. No. 13/220,570, filed Aug. 29, 2011, which claims the benefit of U.S. Provisional Application No. 61/402,574, filed Aug. 30, 2010. The entire disclosure of both applications is incorporated herein by reference in its entirety.

FIELD

The disclosure relates to the field of plant molecular biology and genetic engineering, and specifically to an activation tagging platform for maize and resultant tagged populations and plants therefrom.

PARTIES TO JOINT RESEARCH AGREEMENT

This application describes and claims certain subject matter that was developed under a written joint research agreement between Agrigenetics, Inc., Mycogen Corporation, Exelixis Plant Sciences, Inc., and Exelixis, Inc. having an effective date of Sep. 4, 2007.

BACKGROUND

Common methods of analyzing gene function involve either knocking out gene expression and corresponding gene function, or over-expressing a gene and looking for an associated phenotype.

Conventional mutagenesis techniques frequently result in the identification of loss-of-function mutants and associated gene mutations that interfere with the native gene. However, eukaryotic genomes contain a significant number of functional genes that have redundant coding sequences and regulatory regions within the genome. In addition, such methods do not often result in the identification of genes where loss-of-function results in early lethality. Both of these categories may potentially be identified through a method that results in gain-of-function.

Gain-of-function mutants may result from various mutations in a coding sequence that effect constitutive activation of the resulting protein, or by mutations that alter the level or pattern of gene expression. The latter type of mutations may be the result of altered promoter function in terms of the level of expression, for example, a constitutive versus inducible promoter, tissue or developmental stage specificity of a promoter or other regulatory element or enhanced native promoter activity.

Activation tagging is a method by which genes are randomly and strongly upregulated on a genome-wide scale, after which specific phenotypes can be screened for and selected. Activation tagging is the insertion of transcriptional enhancers randomly throughout a genome in order to increase the transcriptional activity of genes linked to the site of enhancer insertion and/or to down-regulate or inhibit production of functional transcripts from transcription units (coding sequence and regulatory sequences) in which the enhancer has inserted. The transcriptional enhancers may insert near genes, up-regulate their transcription and thereby create altered phenotypes. Lines are considered to be "tagged" because in any individual line the site where the enhancer integrates can be determined and the presence of the enhancer can be associated with a mutant phenotype by genetic analysis.

Activation tagging has been used to activate genes in a variety of plants. An activation T-DNA tagging construct was used to activate genes in tobacco cell culture allowing the cells to grow in the absence of plant growth hormones (Walden et al., *Plant Mol. Biol.* 26: 1521-1528, 1994). A series of publications followed, including reports of genes isolated from plant genomic sequences flanking the T-DNA tag and putatively involved in plant growth hormone responses. (See, e.g., Miklashevichs et al., *Plant J.* 12: 489-498, 1997; Harling et al., *EMBO J.* 16: 5855-5866, 1997; Walden et. al., *EMBO J.* 13: 4729-4736, 1994 and Schell et al., *Trends Plant Sci.* 3: 130, 1998 which discusses investigation of a group of related studies.) In a similar study in *Arabidopsis*, a single gene was isolated from plant genomic DNA by plasmid rescue, identified and found to contain a gene, CKI1, which has been implicated in cytokinin responses in plants, the phenotype of which was confirmed when re-introduced into *Arabidopsis* (Kakimoto, *Science* 274: 982-5, 1996). In a more recent report, activation T-DNA tagging and screening plants for an early flowering phenotype led to the isolation of the FT gene (Kardailsky et al., *Science* 286: 1962-1965, 1999).

Variations of the activation tagging technique include the use of the *Agrobacterium* gene 5 promoter (pg5), which is active only in proliferating cells and must insert directly adjacent to a plant gene in order to influence its expression, using, e.g., the nos promoter/hpt selection cassette (pCVHPT), originally described in Koncz et al., *Proc Natl Acad Sci USA* 86(21): 8467-8471, 1989. Another form of activation tagging utilizes a modified Ds transposon carrying the CaMV 35S promoter and a nos::hpt selection cassette (Wilson et al., *Plant Cell* 8: 659-671, 1996). The modified Ds element is inserted into an antibiotic resistance cassette within a binary vector expression construct. Once introduced into *Arabidopsis*, the transposed Ds element (via the resident 35S promoter) is able to upregulate adjacent plant genes resulting in dominant gain-of-function mutations (Schaffer et al., *Cell* 93: 1219-1229, 1998; Wilson et al., *Plant Cell* 8: 659-671, 1996). Activation tagging vectors have been developed that are useful for screening tens of thousands of transformed plants for morphological phenotypes (Weigel et al., *Plant Physiology*, 122: 1003-1013, 2000).

SUMMARY

Disclosed herein is an activation tagging platform in maize which uses transposon technology that enables transposons located at a few genomic locations and containing the enhancers to be mobilized to near-saturation levels of insertions in the maize genome. This platform can be used to discover genes affecting valuable traits.

In one embodiment, a maize activation tagging DNA construct comprises a coding sequence for a transposase; a detectable reporter encoding region comprising a sequence encoding anthocyanin regulatory gene B-Peru operably linked to a first high level constitutive promoter; and a sequence encoding anthocyanin regulatory gene C1 operably linked to a second high level constitutive promoter; and a non-autonomous transposable T-DNA cassette inserted into the detectable reporter encoding region such that the B-Peru and C1 genes express anthocyanins in a cell containing the maize activation tagging DNA construct only upon excision of the transposable cassette, the transposable cassette comprising a pair of DNA substrates for the transposase, having disposed therebetween a transcriptional enhancer element; and, optionally a sequence encoding a selectable marker operably linked to the transcriptional enhancer element.

In another embodiment, a maize activation tagging DNA construct comprises a coding sequence for maize Spm transposase; a reporter encoding region comprising a sequence encoding anthocyanin regulatory gene B-Peru operably linked to a first globulin 1 promoter; and a sequence encoding anthocyanin regulatory gene C1 operably linked to a second globulin 1 promoter; and a non-autonomous transposable T-DNA cassette inserted into the reporter encoding region such that it disrupts expression of the B-Peru gene, the C1 gene, or both the B-Peru and C1 genes, the transposable cassette comprising the maize 5' and 3' Spm terminal inverted repeats (TIRs), having disposed therebetween the SCBV4X transcriptional enhancer; and, optionally a sequence encoding a selectable marker operably linked to the transcriptional enhancer, wherein Spm-mediated excision of the transposable T-DNA cassette restores expression of the disrupted B-Peru and/or C1 genes.

Also disclosed is a method of generating a tagged population of maize plants, the method comprising transforming a maize plant cell or tissue with any of the disclosed maize activation tagging DNA constructs. Further provided is a tagged population of maize plants produced by the disclosed method. Moreover, a plant cell, kernel, leaf, root, shoot, flower, seed, cutting and other reproductive material useful in sexual or asexual propagation, progeny plants inclusive of F1 hybrids, male-sterile plants and all other plants and plant products derivable from the tagged population of the maize plants are provided.

Also provided is a method of generating a tagged maize plant, the method comprising transforming a maize plant cell or tissue with the construct of any of the disclosed maize activation tagging DNA constructs. In some embodiments, the method further comprises identifying a tagged maize plant by measuring anthocyanin content in a transformed maize plant cell or tissue and comparing anthocyanin content in the transformed maize plant cell or tissue to that in a control maize plant cell or tissue. Moreover, a plant cell, kernel, leaf, root, shoot, flower, seed, cutting and other reproductive material useful in sexual or asexual propagation, progeny plants inclusive of F1 hybrids, male-sterile plants and all other plants and plant products derivable from a tagged maize plant are provided.

The foregoing and other features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A and FIG. 2B illustrate that both B-Peru and C1 gene products are required to synthesize and accumulate anthocyanin pigments in B104. Maize B104 13 days after pollination (DAP), embryos transformed biolistically with Ubi:B-Peru:Nos and Ubi:C1:Nos plasmid DNAs together (FIG. 2A) or Globulin:C1:NOS-Globulin:B-Peru:Nos single plasmid DNA (FIG. 2B) showed anthocyanin accumulation. The respective engineered expression cassettes are illustrated above each panel.

FIG. 3A illustrates the biochemical and molecular analyses of the Spm-dependent dSpm-excision in B104 maize. FIG. 3A is a photograph of B104 embryos that were transformed with LBA4404-pEPS3004 plasmid 13-days after pollination (DAP). Arrow indicates anthocyanin accumulation.

FIG. 3B is a pair of agarose gels, illustrating the results of genomic PCR analysis to show empty donor site (EDS). Lane 1, Genomic DNA isolated from the pooled purple tissues of B104 embryos transformed with LBA4404-pEPS3004. Lane 2, Genomic DNA isolated from the B104 embryos transformed with LBA4404-pEPS6002, a GUS construct. Lane 3, Genomic DNA isolated from the B104 embryos transformed with cocultivation buffer. M, 100 bp ladder. Top panel shows PCR using primers flanking the dSpm unit of the pEPS3004. Bottom panel shows endogenous GAPDH genomic PCR.

FIG. 3C provides the sequences resulting from sequence analysis of the EDS (FDS, EDS 1, EDS 2, EDS 3, EDS 4, EDS 5 and EDS 6 sequences are set forth herein as SEQ ID NO: 3, SEQ ID NO: 4, SEQ ID NO: 5, SEQ ID NO: 6, SEQ ID NO: 7, SEQ ID NO: 8 and SEQ ID NO: 9, respectively). The EDS-specific PCR product was cloned into a TOPO vector and transformed into *E. coli*. Plasmid DNA was prepared from 47 colonies and sequenced. The red dots and circled red letters indicate base pair deletion and transition, respectively, in the EDS sites; the sequences are also listed in Table 2. EDS, empty donor site; FDS, Full donor site.

FIG. 5 is a series of photographs of ears of corn (maize), illustrating T1 seed phenotypes of plants containing the ZeaTAG element. All yellow kernels indicate no transposition, yellow and purple kernels indicate early germinal transposition (identical photo to FIG. 4), yellow kernels and yellow kernels with purple sectors indicate somatic transposition and purple kernels indicate somatic and late germinal transposition. In the figures, the dark coloration is purple and the light coloration is yellow.

SEQUENCES LISTING

Figure 1:
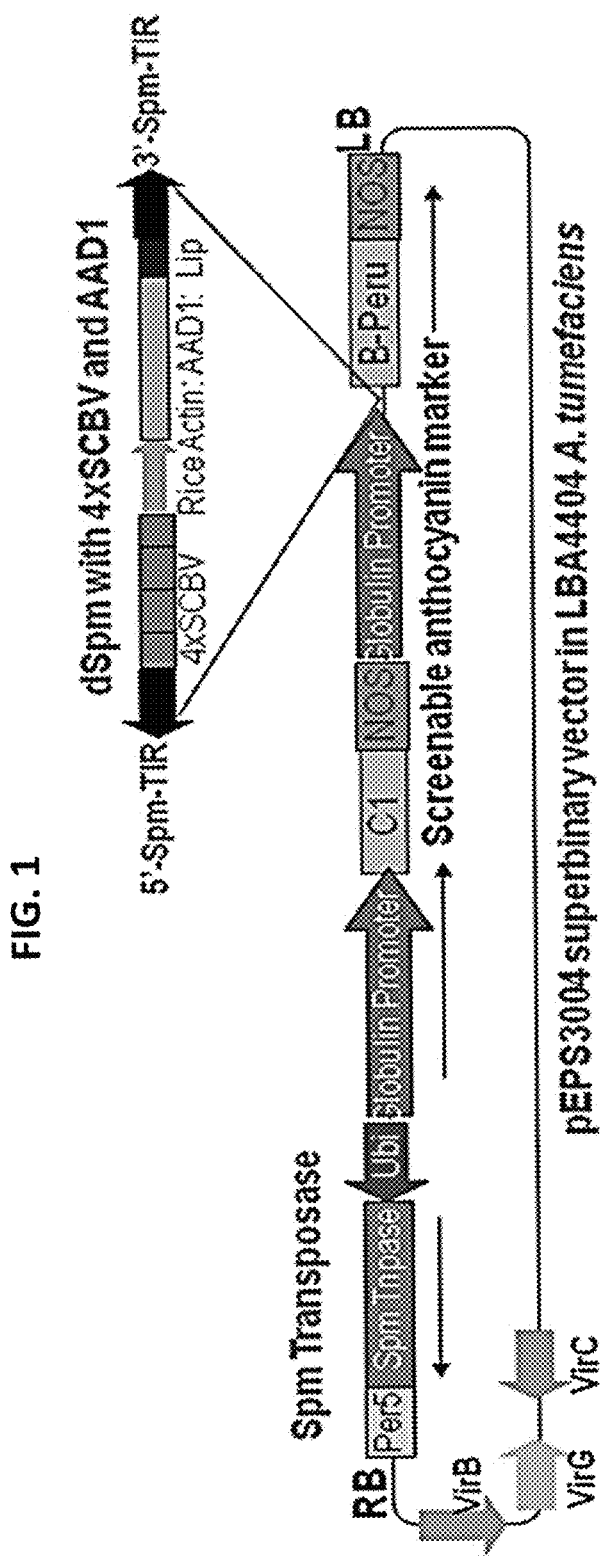
FIG. 1 shows a schematic drawing of pEPS3004, an example Spm-ZeaTAGvector.

The nucleic and/or amino acid sequences listed in this disclosure and/or in the accompanying Sequence Listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. Nucleic acid sequences are presented in the standard 5' to 3' direction.

The Sequence Listing is submitted herewith as an ASCII compliant text file named "Sequences.txt", created on Dec. 5, 2014, and having a size of ~40.0 kilobytes, as permitted under 37 CFR §1.821(c). The material in the aforementioned file is hereby incorporated by reference in its entirety.

SEQ ID NO: 1 is the nucleic acid sequence of a portion of pEPS3004, containing the following elements:

| Bases of SEQ ID NO: 1 | Description |
|---|---|
| 1 to 25 | T-DNA Right Border Repeat sequence as provided by the pSB11 vector. |
| 118 to 482 | Maize (*Zea mays*) Per5 transcription terminator region as disclosed in U.S. Pat. No. 6,699,984. |
| 491 to 8132 | Essentially the complement of the sequence comprising the coding sequences of TpnA and TpnD of a maize Spm transposase as disclosed by bases 400 to 8045 of GenBank Accession No. M25427.1\|MZETNENSPM. |
| 8137 to 10127 | Essentially the complement of the maize ubiquitin1 promoter and associated intron 1 as disclosed in U.S. Pat. No. U.S. Pat. No. 5,510,474 and bases 7 to 1990 of GenBank Accession No. S94464.1. |
| 10169 to 11417 | Promoter region of a maize globulin gene (essentially bases 2 to 1401 as disclosed in GenBank Accession No. L22344.1) |
| 11422 to 12374 | Encompasses a maize C1 protein coding sequence, which comprises bases 11440 to 12261, (essentially as disclosed in GenBank Accession No. AF320614) |
| 12390 to 12643 | Nopaline synthase transcription terminator region as disclosed in bases 1847 to 2103 of GenBank Accession No. V00087.1. |
| 12703 to 13951 | Promoter region of a maize globulin gene (essentially bases 2 to 1401 as disclosed in GenBank Accession No. L22344.1) |
| 13982 to 14251 | En-I 5' terminal inverted repeat as disclosed by bases 1 to 270 of GenBank Accession No. M25427.1\|MZETNENSPM |
| 15020 to 15301 | SCBV promoter activator element copy #1 |
| 15314 to 15595 | SCBV promoter activator element copy #2 |
| 15608 to 15889 | SCBV promoter activator element copy #3 |
| 15902 to 16183 | SCBV promoter activator element copy #4 |
| 16272 to 17668 | Rice (*Oryza sativa*) actin promoter with associated intron 1 and 5' UTR (essentially as disclosed as bases 12 to 1411 of GenBank Accession No. EU155408.1) |
| 17671 to 18561 | Coding sequence for AAD-1 herbicide tolerance gene as disclosed in US Patent Application No. 20090093366 |
| 18588 to 18944 | 3' Transcription terminator sequence from maize lipase gene essentially as disclosed as bases 921 to 1277 of GenBank Accession No. gb\|L35913.1\|MZELIPASE and in U.S. Pat. No. 7,179,902- |
| 19520 to 20160 | En-I 3' terminal inverted repeat as disclosed by bases 7647 to 8287 of GenBank Accession No. M25427.1\|MZETNENSPM |
| 20191 to 22109 | Encompasses a maize B-Peru (BP) protein coding sequence, which comprises bases 20214 to 21905, (essentially bases 121 to 1970 of GenBank Accession No. X57276.1\|) |
| 22125 to 22378 | Nopaline synthase transcription terminator region as disclosed in bases 1847 to 2103 of GenBank Accession No. V00087.1. |
| 22497 to 22521 | T-DNA Left border repeat sequence as provided by the pSB11 vector. |

SEQ ID NO: 2 is a transcriptional activator element derived from a promoter found in the genome of a Sugar Cane Bacilliform Virus (SCBV).

SEQ ID NO: 3 is a partial nucleic acid sequence of pEPS3004 DS including an artificial transposon (corresponding to positions 13982-20160 of SEQ ID NO: 1).

SEQ ID NOs: 4-9 are nucleic acid sequences after transposition of an artificial transposon.

SEQ ID NOs: 10-11 are oligonucleotide primers.

DETAILED DESCRIPTION

I. Abbreviations

AAD aryloxyalkanoate dioxygenase
bp base pairs
BP B-Peru
DS donor site
EDS empty donor site
FDS full donor site
IP intervening bases
PCR polymerase chain reaction
SCBV sugar cane bacilliform virus
T-DNA transfer DNA
Ti tumor inducing
TIR terminal invert repeat II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

5' and/or 3': Nucleic acid molecules (such as, DNA and RNA) are said to have "5' ends" and "3' ends" because mononucleotides are reacted to make polynucleotides in a manner such that the 5' phosphate of one mononucleotide pentose ring is attached to the 3' oxygen of its neighbor in one direction via a phosphodiester linkage. Therefore, one end of a polynucleotide is referred to as the "5' end" when its 5' phosphate is not linked to the 3' oxygen of a mononucleotide pentose ring. The other end of a polynucleotide is referred to as the "3' end" when its 3' oxygen is not linked to a 5' phosphate of another mononucleotide pentose ring. Notwithstanding that a 5' phosphate of one mononucleotide pentose ring is attached to the 3' oxygen of its neighbor, an internal nucleic acid sequence also may be said to have 5' and 3' ends.

In either a linear or circular nucleic acid molecule, discrete internal elements are referred to as being "upstream" or 5' of the "downstream" or 3' elements. With regard to DNA, this terminology reflects that transcription proceeds in a 5' to 3' direction along a DNA strand. Promoter and enhancer elements, which direct transcription of a linked gene, are generally located 5' or upstream of the coding region. However, enhancer elements can exert their effect even when located 3' of the promoter element and the coding region. Transcription termination and polyadenylation signals are located 3' or downstream of the coding region.

Activation Tagging: A process by which a heterologous nucleic acid construct including an enhancer element, is inserted into a plant genome. The enhancer element can act to enhance transcription of a single gene or may enhance transcription of two or more genes at the same time. The "tag" is a region of the heterologous nucleic acid construct (e.g. the vector) which may be used to locate and thereby identify and characterize an introduced nucleic acid sequence that has integrated in the plant genome. An Activation Tagging DNA construct is a DNA construct that provides exemplary mutagens for generating both loss-of-function and gain-of-function in plants. Activation tagging nucleic acid constructs may be stably introduced into a plant genome in order to enhance expression of native (endogenous) plant genes. (See, e.g., Walden et al., *Plant Mol. Biol.* 26(5): 1521-1528, 1994 Weigel et al., *Plant Physiology,* 122: 1003-1013, 2000). In one example, an activation tagging DNA construct is a maize activation tagging DNA construct. In a particular example, an activation tagging DNA construct has a nucleic acid sequence corresponding to that set forth in SEQ ID NO.: 1 (pEPS3004 T-DNA sequence from right border to left border).

Agronomic trait: Characteristic of a plant, which characteristics include, but are not limited to, plant morphology, physiology, growth and development, yield, nutritional enhancement, disease or pest resistance, or environmental or chemical tolerance. An "enhanced agronomic trait" refers to a measurable improvement in an agronomic trait including, but not limited to, yield increase, including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also affected by efficiency of germination (including germination in stressed conditions), growth rate (including growth rate in stressed conditions), ear number, seed number per ear, seed size, composition of seed (starch, oil, protein) and characteristics of seed fill. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this disclosure can also be used to provide plants having improved growth and development, and ultimately increased yield, as the result of modified expression of plant growth regulators or modification of cell cycle or photosynthesis pathways. Additional examples of agronomic traits, and altering such traits in plants, are provided herein and/or will be recognized by those of ordinary skill in the art.

Amplification: When used in reference to a nucleic acid, this refers to techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Anthocyanins: A group of water-soluble flavonoids that impart pink/red to purple color to leaves and other organs of plants. Common anthocyanins include derivatives of cyanidin, delphinidin, malvidin and pelargonidin. In an example, anthocyanin pigments are pigments with an absorption spectra at 520 nm.

Cassette: A manipulable fragment of DNA carrying (and capable of expressing) one or more genes of interest between one or more sets of restriction sites. A cassette can be transferred from one DNA sequence (usually on a vector) to another by 'cutting' the fragment out using restriction enzymes and 'pasting' it back into the new context.

A transposable cassette is one that is capable of transferring or moving within a gene, a chromosome or a genome by a transposase. In one example, a transposable cassette includes a pair of DNA substrates for the transposase, having disposed therebetween a transcriptional enhancer; and, optionally a sequence encoding a selectable marker operably linked to the transcriptional enhancer.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells or other samples.

Construct: Any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more transcribable polynucleotide molecule has been operably linked.

Control plant: A plant that does not contain a recombinant DNA that confers (for instance) an enhanced or altered agronomic trait in a transgenic plant, is used as a baseline for comparison, for instance in order to identify an enhanced or altered agronomic trait in the transgenic plant. A suitable control plant may be a non-transgenic plant of the parental line used to generate a transgenic plant, or a plant that at least is non-transgenic for the particular trait under examination (that is, the control plant may have been engineered to contain other heterologous sequences or recombinant DNA molecules). Thus, a control plant may in some cases be a transgenic plant that comprises an empty vector or marker gene, but does not contain the recombinant DNA, or does not contain all of the recombinant DNAs, in the test plant.

DNA (deoxyribonucleic acid): DNA is a long chain polymer which comprises the genetic material of most organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule includes the reverse complement of that DNA molecule. Except where single-strandedness is required by the text herein, DNA molecules, though written to depict only a single strand, encompass both strands of a double-stranded DNA molecule.

Encode: A polynucleotide is said to encode a polypeptide if, in its native state or when manipulated by methods known to those skilled in the art, the polynucleotide molecule can be transcribed and/or translated to produce a mRNA for and/or the polypeptide or a fragment thereof. The anti-sense strand is the complement of such a nucleic acid, and the encoding sequence can be deduced therefrom.

Enhancer domain: A cis-acting transcriptional regulatory element (a.k.a. cis-element) that confers an aspect of the overall control of gene expression. An enhancer domain may function to bind transcription factors, which are trans-acting protein factors that regulate transcription. Some enhancer domains bind more than one transcription factor, and transcription factors may interact with different affinities with more than one enhancer domain. Enhancer domains can be identified by a number of techniques, including deletion analysis (deleting one or more nucleotides from the 5' end or internal to a promoter); DNA binding protein analysis using DNase I foot printing, methylation interference, electrophoresis mobility-shift assays, in vivo genomic foot printing by ligation-mediated PCR, and other conventional assays; or by DNA sequence comparison with known cis-element motifs using conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from promoters that include such elements, and they can be synthesized with additional flanking nucleotides that contain useful restriction enzyme sites to facilitate subsequence manipulation.

(Gene) Expression: Transcription of a DNA molecule into a transcribed RNA molecule. More generally, gene expression encompasses the processes by which a gene's coded information is converted into the structures present and operating in the cell. Expressed genes include those that are transcribed into mRNA and then translated into protein and those that are transcribed into RNA but not translated into protein (for example, siRNA, transfer RNA and ribosomal RNA). Thus, expression of a target sequence, such as a gene or a promoter region of a gene, can result in the expression of an mRNA, a protein, or both. The expression of the target sequence can be inhibited or enhanced (decreased or increased). Gene expression may be described as related to temporal, spatial, developmental, or morphological qualities as well as quantitative or qualitative indications.

Gene regulatory activity: The ability of a polynucleotide to affect transcription or translation of an operably linked transcribable polynucleotide molecule. An isolated polynucleotide molecule having gene regulatory activity may provide temporal or spatial expression or modulate levels and rates of expression of the operably linked transcribable polynucleotide molecule. An isolated polynucleotide molecule having gene regulatory activity may include a promoter, intron, leader, or 3' transcription termination region.

Genetic material: A phrase meant to include all genes, nucleic acid, DNA and RNA.

Isolated: An "isolated" biological component (such as a nucleic acid, peptide or protein) has been substantially separated, produced apart from, or purified away from other biological components in the cell of the organism in which the component naturally occurs, e.g., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Maize (*Zea mays*): Maize, or corn, is a monocotyledonous plant, being a member of the grass family. Maize has a distinct growth form; the lower leaves being like broad flags, 50-100 centimeters long and 5-10 centimeters wide (2-4 ft by 2-4 in); the stems are erect, conventionally 2-3 meters (7-10 ft) in height, with many nodes, casting off flag-leaves at every node. Under these leaves and close to the stem grow the ears. They grow about 3 millimeters a day. Certain varieties of maize have been bred to produce many additional developed ears. The kernel of maize has a pericarp of the fruit fused with the seed coat, typical of the grasses, and the entire kernel is often referred to as the seed. The cob is close to a multiple fruit in structure, except that the individual fruits (the kernels) never fuse into a single mass. The grains (kernels) are about the size of peas, and adhere in regular rows around a white pithy substance, which forms the ear. An ear contains from 200 to 400 kernels, and is from 10-25 centimeters (4-10 inches) in length. They are of various colors: blackish, bluish-gray, purple, green, red, white and yellow.

Operably linked: This term refers to a juxtaposition of components, particularly nucleotide sequences, such that the normal function of the components can be performed. Thus, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. A coding sequence that is "operably linked" to regulatory sequence(s) refers to a configuration of nucleotide sequences wherein the coding sequence can be expressed under the regulatory control (e.g., transcriptional and/or translational control) of the regulatory sequences.

Optional: "Optional" or "optionally" means that the subsequently described event or circumstance can but need not occur, and that the description includes instances where said event or circumstance occurs and instances where it does not.

ORF (open reading frame): A series of nucleotide triplets (codons) coding for amino acids without any termination codons. These sequences are usually translatable into a peptide.

Percent sequence identity: The percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted using tools such as the local homology algorithm of Smith and Waterman, the homology alignment algorithm of Needleman and Wunsch, the search for similarity method of Pearson and Lipman. Such comparisons are preferably carried out using the computerized implementations of these algorithms, such as GAP, BEST-FIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment (that is, the entire reference sequence or a smaller defined part of the reference sequence). Percent sequence identity is represented as the identity fraction multiplied by 100. The comparison of one or more polynucleotide sequences may be to a full-length polynucleotide sequence or a portion thereof, or to a longer polynucleotide sequence. Substantial percent sequence identity is at least about 80% sequence identity, at least about 90% sequence identity, or even greater sequence identity, such as about 98% or about 99% sequence identity.

Plant: Any plant and progeny thereof. The term also includes parts of plants, including seed, cuttings, tubers, fruit, flowers, etc. In various embodiments, the term plant refers to cultivated plant species, such as corn, cotton, canola, sunflower, soybeans, sorghum, alfalfa, wheat, rice, plants producing fruits and vegetables, and turf and ornamental plant species. The term plant cell, as used herein, refers to the structural and physiological unit of plants, consisting of a protoplast and the surrounding cell wall. The term plant organ, as used herein, refers to a distinct and visibly differentiated part of a plant, such as root, stem, leaf or embryo.

More generally, the term plant tissue refers to any tissue of a plant in planta or in culture. This term includes a whole plant, plant cell, plant organ, protoplast, cell culture, or any group of plant cells organized into a structural and functional unit.

Polynucleotide molecule: Single- or double-stranded DNA or RNA of genomic or synthetic origin; that is, a polymer of deoxyribonucleotide or ribonucleotide bases, respectively, read from the 5' (upstream) end to the 3' (downstream) end.

Polypeptide molecule: A polymer in which the monomers are amino acid residues which are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

Promoter: An array of nucleic acid control sequences which direct transcription of a nucleic acid, by recognition and binding of e.g., RNA polymerase II and other proteins (trans-acting transcription factors) to initiate transcription. A promoter includes necessary nucleic acid sequences near the start site of transcription, such as, in the case of a polymerase II type promoter, a TATA element. Minimally, a promoter typically includes at least an RNA polymerase binding site together with one or more transcription factor binding sites which modulate transcription in response to occupation by transcription factors. Representative examples of promoters (and elements that can be assembled to produce a promoter) are described herein. Promoters may be defined by their temporal, spatial, or developmental expression pattern.

A plant promoter is a native or non-native promoter that is functional in plant cells. In one example, a promoter is a high level constitutive promoter, such as a tissue specific promoter (e.g., globulin 1 promoter which is expressed in aleurone tissues).

Protein: A biological molecule, for example a polypeptide, expressed by a gene and comprised of amino acids.

Protoplast: An isolated plant cell without cell walls, having the potential for regeneration into cell culture or a whole plant.

Purified: The term purified does not require absolute purity; rather, it is intended as a relative term. Thus, for example, a purified protein preparation is one in which the protein is more enriched than the protein is in its generative environment, for instance within a cell or in a biochemical reaction chamber. Preferably, a preparation of protein is purified such that the protein represents at least 50% of the total protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Similarly, a recombinant protein is one encoded for by a recombinant nucleic acid molecule.

Regulatable promoter: A promoter the activity of which is regulated (directly or indirectly) by an agent, such as a transcription factor, a chemical compound, an environmental condition, or a nucleic acid molecule.

Regulating gene expression: Processes of controlling the expression of a gene by increasing or decreasing the expression, production, or activity of an agent that affects gene expression. The agent can be a protein, such as a transcription factor, or a nucleic acid molecule, such as a miRNA or an siRNA molecule, which when in contact with the gene or its upstream regulatory sequences, or a mRNA encoded by the gene, either increases or decreases gene expression.

Regulatory sequences or elements: These terms refer generally to a class of polynucleotide molecules (such as DNA molecules, having DNA sequences) that influence or control transcription or translation of an operably linked transcribable polynucleotide molecule, and thereby expression of genes. Included in the term are promoters, enhancers, leaders, introns, locus control regions, boundary elements/ insulators, silencers, Matrix attachment regions (also referred to as scaffold attachment regions), repressor, transcriptional terminators (a.k.a. transcription termination regions), origins of replication, centromeres, and meiotic recombination hotspots. Promoters are sequences of DNA near the 5' end of a gene that act as a binding site for RNA polymerase, and from which transcription is initiated. Enhancers are control elements that elevate the level of transcription from a promoter, usually independently of the enhancer's orientation or distance from the promoter. Locus control regions (LCRs) confer tissue-specific and temporally regulated expression to genes to which they are linked. LCRs function independently of their position in relation to the gene, but are copy-number dependent. It is believed that they function to open the nucleosome structure, so other factors can bind to the DNA. LCRs may also affect replication timing and origin usage. Insulators (also known as boundary elements) are DNA sequences that prevent the activation (or inactivation) of transcription of a gene, by blocking effects of surrounding chromatin. Silencers and repressors are control elements that suppress gene expression; they act on a gene independently of their orientation or distance from the gene. Matrix attachment regions (MARs), also known as scaffold attachment regions, are sequences within DNA that bind to the nuclear scaffold. They can affect transcription, possibly by separating chromosomes into regulatory domains. It is believed that MARs mediate higher-order, looped structures within chromosomes. Transcriptional terminators are regions within the gene vicinity that RNA polymerase is released from the template. Origins of replication are regions of the genome that, during DNA synthesis or replication phases of cell division, begin the replication process of DNA. Meiotic recombination hotspots are regions of the genome that recombine more frequently than the average during meiosis. Specific nucleotides within a regulatory region may serve multiple functions. For example, a specific nucleotide may be part of a promoter and participate in the binding of a transcriptional activator protein.

Isolated regulatory elements that function in cells (for instance, in plants or plant cells) are useful for modifying plant phenotypes, for instance through genetic engineering.

RNA: A typically linear polymer of ribonucleic acid monomers, linked by phosphodiester bonds. Naturally occurring RNA molecules fall into three general classes, messenger (mRNA, which encodes proteins), ribosomal (rRNA, components of ribosomes), and transfer (tRNA, molecules responsible for transferring amino acid monomers to the ribosome during protein synthesis). Messenger RNA includes heteronuclear (hnRNA) and membrane-associated polysomal RNA (attached to the rough endoplasmic reticulum). Total RNA refers to a heterogeneous mixture of all types of RNA molecules.

Screenable Marker: A marker that confers a trait identified through observation or testing.

Selectable Marker: A marker that confers a trait that one can select for by chemical means, e.g., through the use of a selective agent (e.g., an herbicide, antibiotic, or the like). Selectable markers include but are not limited to antibiotic resistance genes, such as, kanamycin (nptII), G418, bleomycin, hygromycin, chloramphenicol, ampicillin, tetracycline, or the like. Additional selectable markers include a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance; or a methotrexate resistant DHFR gene. In one example, the selectable marker is AAD1.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs of a sequence disclosed or referred to herein will possess a relatively high degree of sequence identity when aligned using standard methods.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS.* USA 85: 2444, 1988); Higgins and Sharp (*Gene*, 73: 237-244, 1988); Higgins and Sharp (*CABIOS* 5: 151-153, 1989); Corpet et al. (*Nuc. Acids Res.* 16: 10881-90, 1988); Huang et al. (*Comp. Appls Biosci.* 8: 155-65, 1992); and Pearson et al. (*Methods in Molecular Biology* 24: 307-31, 1994). Altschul et al. (*Nature Genet.*, 6: 119-29, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at with a web address of biology.ncsa.uiuc.edu.

Orthologs or paralogs (more generally, homologs) of a specified sequence are typically characterized by possession of greater than 75% sequence identity counted over the full-length alignment with the amino acid sequence of a specified protein (or the nucleic acid sequence of a specified nucleic acid molecule) using ALIGN set to default parameters. Sequences with even greater similarity to the reference sequences will show increasing percentage identities when assessed by this method, such as at least 80%, at least 85%, at least 90%, at least 92%, at least 95%, or at least 98% sequence identity. In such an instance, percentage identities will be essentially similar to those discussed for full-length sequence identity.

When significantly less than the entire sequence is being compared for sequence identity, homologs will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods are described at web address of biology.ncsa.uiuc.edu. One of skill in the art will appreciate that these sequence identity ranges are provided for guidance only; it is entirely possible that strongly significant homologs could be obtained that fall outside of the ranges provided. The present disclosure provides not only the peptide homologs that are described above, but also nucleic acid molecules that encode such homologs.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual*, Cold Spring Harbor, N.Y., 1989) and Tijssen (*Laboratory Techniques in Biochemistry and Molecular Biology* Part I, Ch. 2, Elsevier, New York, 1993). Nucleic acid molecules that hybridize under stringent conditions to a specified protein sequence will typically hybridize to a probe based on either the protein encoding sequence, an entire domain, or other selected portions of the encoding sequence under wash conditions of 0.2×SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Substrate: A molecule upon which an enzyme acts. In one example, a substrate is a DNA substrate for a transposase (e.g., 5' and 3' terminal inverted repeats (TIRs) of the maize Spm transposable element).

Terminal Inverted Repeats: Related or identical sequences of DNA in inverted form occurring at opposite ends of some transposons. A terminal inverted repeat can be a 5' or 3' terminal inverted repeat, such as a 5' or 3' terminal inverted repeat of maize Spm transposable element.

Transposase: An enzyme that binds to the ends of a transposon and catalyzes the movement of the transposon to another part of the genome by a "cut" and "paste" mechanism or a replicative transposition mechanism.

Transposons: A nucleotide sequence such as a DNA or RNA sequence that is capable of transferring location or moving within a gene, a chromosome or a genome. Exemplary transposons such as Ac, Ds, Mu and Spm are elements that can insert themselves into genes and cause mutations. The mutations may be unstable due to subsequent excision of the transposon from the mutant locus during plant or seed development. (See, e.g., Doring, H. P. and Starlinger *Ann. Rev. Genet.* 20: 175-200, 1986; Federoff, N. "Maize Transposable Elements" in Mobile DNA. Wowe, M. M. and Berg, D. E., eds., *Amer. Soc. Microbiol., Wash., D.C., pp.* 377-411, 1989) An exemplary transposon-tagging strategy used to identify a semi-dominant mutation affecting plant height, hypocotyl elongation, and fertility has been described (see Wilson K et al., *Plant Cell* 8(4): 659-71, 1996). Transposon sequences may be incorporated into an activation tagging nucleic acid construct in order to move an enhancer around the plant genome. Transposons are alternatively referred to as transposable elements.

Transgenic plant: A plant that contains a foreign (heterologous) nucleotide sequence inserted into either its nuclear genome or organellar genome.

Transgene: A nucleic acid sequence that is inserted into a host cell or host cells by a transformation technique.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

For designations of nucleotide residues of polynucleotides, DNA, RNA, oligonucleotides, and primers, and for designations of amino acid residues of proteins, standard IUPAC abbreviations are employed throughout this document.

Unless otherwise explained, all technical and scientific terms used herein have the same meaning as commonly understood by one of ordinary skill in the art to which this invention belongs. Unless otherwise indicated, molecular biological and biochemical manipulations described were performed by standard methodologies as disclosed in, for example, Sambrook et al. (In *Molecular Cloning: A Laboratory Manual*, Cold Spring Harbor, N.Y., 1989) and Tijssen (*Laboratory Techniques in Biochemistry and Molecular Biology* Part I, Ch. 2, Elsevier, New York, 1993), and updates thereof through the filing date of this application. Unless specifically indicated or implied, the terms "a", "an", and "the" signify "at least one" as used herein. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. All percentages are by weight and all solvent mixture proportions are by volume unless otherwise noted. All temperatures are in degrees Celsius.

Although methods and materials similar or equivalent to those described herein can be used in the practice or testing of the present invention, suitable methods and materials are described below. All publications, patent applications, patents, and other references mentioned herein are incorporated by reference in their entirety to the extent they are not inconsistent with the explicit teachings of this specification. In case of conflict, the present specification, including explanations of terms, will control. In addition, the materials, methods, and examples are illustrative only and not intended to be limiting.

III. Overview of Several Embodiments

Disclosed herein is an activation tagging platform in maize which uses transposon technology that enables transposons located at a few genomic locations and containing the enhancers to be mobilized to near-saturation levels of insertions in the maize genome. This platform can be used to discover genes affecting valuable traits.

In one embodiment, a maize activation tagging DNA construct comprises a coding sequence for a transposase; a detectable reporter encoding region comprising a sequence encoding anthocyanin regulatory gene B-Peru operably linked to a first high level constitutive promoter; and a sequence encoding anthocyanin regulatory gene C1 operably linked to a second high level constitutive promoter; and a non-autonomous transposable T-DNA cassette inserted into the detectable reporter encoding region such that the B-Peru and C1 genes express anthocyanins in a cell containing the maize activation tagging DNA construct only upon excision of the transposable cassette, the transposable cassette comprising a pair of DNA substrates for the transposase, having disposed therebetween a transcriptional enhancer element; and, optionally, a sequence encoding a selectable marker operably linked to the transcriptional enhancer. In one example, the pair of DNA substrates for the transposase is the 5' and 3' terminal inverted repeats (TIRs) of the maize Spm transposable element, and the transposase is maize Spm. In some embodiments, the transcriptional enhancer element comprises at least two copies of a SCBV enhancer. In one particular example, the transcriptional enhancer element comprises four copies of a SCBV enhancer. In some examples, the maize activation tagging DNA construct comprises a first and/or a second high level constitutive promoter which is a tissue specific promoter. In other examples, the maize activation tagging DNA construct includes a first and/or a second high level constitutive tissue specific promoter which is a globulin 1 promoter. In some examples, the maize activation tagging DNA construct includes the selectable marker AAD1.

In one particular embodiment, a disclosed maize activation tagging DNA has a nucleic acid sequence as set forth by SEQ ID NO: 1.

In another embodiment, a maize activation tagging DNA construct comprises a coding sequence for maize Spm transposase; a reporter encoding region comprising a sequence encoding anthocyanin regulatory gene B-Peru operably linked to a first globulin 1 promoter; and a sequence encoding anthocyanin regulatory gene C1 operably linked to a second globulin 1 promoter; and a non-autonomous transposable T-DNA cassette inserted into the reporter encoding region such that it disrupts expression of the B-Peru gene, the C1 gene, or both the B-Peru and C1 genes, the transposable cassette comprising the maize 5' and 3' Spm terminal inverted repeats (TIRs), having disposed therebetween the SCBV4X transcriptional enhancer; and, optionally a sequence encoding a selectable marker operably linked to the transcriptional enhancer, wherein Spm-mediated excision of the transposable T-DNA cassette restores expression of the disrupted B-Peru and/or C1 genes.

Also provided are methods of generating a tagged population of maize plants. In one embodiment, the disclosed method comprises transforming a maize plant cell or tissue with any one of the disclosed DNA constructs. In some embodiments, the method further comprises identifying a tagged population of maize plants. In one example, identifying a tagged population of maize plants comprises measuring anthocyanin content in a transformed maize plant cell or tissue and comparing anthocyanin content in the transformed maize plant cell or tissue to that in a control maize plant cell or tissue. In another example, identifying a tagged population of maize plants comprises identifying germinal transposition, somatic transposition or a combination thereof in the tagged population Also disclosed is a tagged population of maize plants produced by any of the disclosed methods. Additional embodiments provide a plant cell, kernel, leaf, root, shoot, flower, seed, cutting and other reproductive material useful in sexual or asexual propagation, progeny plants inclusive of F1 hybrids, male-sterile plants and all other plants and plant products derivable from a disclosed tagged population of maize plants.

IV. Activation Tagging

Activation tagging is a process by which a heterologous nucleic acid construct comprising an enhancer element is inserted into a plant genome. The enhancer element can act to enhance transcription of a single gene or may enhance transcription of two or more genes at the same time. The "tag" is a region of the heterologous nucleic acid construct (e.g. the vector) which may be used to locate and thereby identify and characterize an introduced nucleic acid sequence that has integrated in the plant genome. Activation tagging nucleic acid constructs may be stably introduced into a plant genome in order to enhance expression of native (endogenous) plant genes. (See, e.g., Walden et al., *Plant Mol Biol* 26(5), 1521-8, 1994 Weigel et al., *Plant Physiology*, 122: 1003-1013, 2000). Activation tagging has been used in many different organisms including *Arabidopsis*, tomato, rice, petunia and barley (Weigel et al., *Plant Physiol*. 122: 1003-1014, 2000; Jeong et al., *Plant Physiol*. 130: 1636-1644, 2002, First published Dec. 1, 2002, 10.1104/pp. 014357; Zubko et al., *The Plant Journal* 29: 797-808, 2002; Ayliffe et al., *Plant Mol. Biol.* 64: 329-347, 2007; Mathews et al., *Plant Cell* 15: 1689-1703, 2003). It has been used to identify genes affecting multiple plant traits. To date, no activation tagged population of maize has been described.

Disclosed herein is an activation tagged population in maize that can be used to discover genes affecting valuable traits. The maize genome is approximately 2500 Mbp, but the genes are clustered in islands of "gene-rich" regions that total approximately 450 Mbp (Myers et al., *Genome Research* 11: 1660-1676, 2001; Wendl et al., *Bioinformatics* 6: 245-257, 2005). A population of activation tagged plants that has a high probability of activating all maize genes requires approximately 100,000 individual insertion events. To generate such a large maize activation tagged population, the inventors have developed a strategy using transposon technology. Modified transposons can be used to amplify the number of insertion events generated from a few primary transformants (Marsch-Martinez et al., *Plant Physiol.* 129: 1544-1556, 2002; Kumar et al., *Plant J.* 44: 879-892, 2005). Because almost 80% of the maize genome is composed of repetitive DNA, the activation tagging element needs to integrate preferentially into "gene-rich" regions and transposons have been shown to do so (Tissier et al., *Plant Cell* 11: 1841-1852, 1999; Speulman et al., *Plant Cell* 11: 1853-1866, 1999; Greco et al., *Mol. Gen. Genet.* 270: 514-523, 2004).

In one embodiment, the disclosed activation tagging DNA construct utilizes a maize transposon to amplify the activation tagging population. For example, an exemplary activation tagging DNA construct includes the following components: (1) a coding sequence for a transposase; (2) a detectable reporter encoding region; and (3) a non-autonomous transposable T-DNA cassette. In one exemplary embodiment of the disclosed platform, the non-autonomous transposable T-DNA cassette is inserted into the detectable reporter encoding region such that the regulatory genes (such as B-Peru and C1 genes) express the detectable marker (such as anthocyanins) in a cell containing the maize activation tagging DNA construct only upon excision of the transposable cassette.

In one example, an exemplary construct includes a maize enhancer or suppressor-mutator (En/Spm) transposon of maize to amplify the activation tagging population. The construct also contains a transcriptional enhancer element comprised of four copies of a sugarcane baciliiform virus (SCBV) enhancer and an AAD1 selectable marker which have been cloned between the terminal inverted repeats (TIRs) of the Spm transposable element. This is a non-autonomous transposon that requires a transposase in order to "hop". The Spm transposase is located on the same transformation vector but outside the TIRs of the transposon. When the transposon is mobilized by the transposase, it will likely move to a location that is not closely linked with the transposase (FIG. 1). Transposition is monitored by use of a screenable marker comprising the anthocyanin regulatory genes B-Peru and C1. The B-Peru (BP) and the C1 genes in these constructs are under the regulation of a maize globulin promoter (a promoter that is expressed in aleurone tissues of a seed).

In one particular embodiment, an exemplary construct is arranged so that the B-Peru coding region is downstream (in the transcriptional sense) from a copy of a maize globulin1 promoter, but is displaced from it by 6256 bases of intervening DNA. These intervening bases (herein called IB) prevent the transcription of a functional mRNA encoding the BP protein, initiated by the globulin1 promoter. Thus, in order for the BP protein to be produced under the control of the second copy of the globulin promoter, the IB must be removed in such a fashion that results in creation of an active gene (e.g., by appropriate juxtaposition of the globulin1 promoter and BP protein coding region). Further, the IB comprises an artificial transposon partially derived from elements of the maize En/Spm transposon. In the native En/Spm transposon system, transposase proteins TpnA and TpnD encoded by Spm act on 5' and 3' Terminal Inverted Repeat (TIR) sequences to mobilize the transposon via excision from a donor chromosomal locus and insertion into distal locations. The 6256 bp of the IB separating the globulin promoter and BP coding region include the 5' and 3' TIR sequences that flank an active gene encoding a plant selectable marker protein (AAD1), under the expression control of a (constitutive) rice actin promoter (FIG. 1). Thus, the artificial transposon of this particular example comprises a pair of TIR elements which flank a plant selectable marker gene. Four tandem copies of a transcriptional activator element (SEQ ID NO: 2) derived from a promoter found in the genome of a SCBV is positioned between the 5' TIR element and the rice actin promoter that controls expression of the AAD1 gene (see FIG. 1).

The T-DNA of pEPS3004 as disclosed in SEQ ID NO: 1 and FIG. 1 integrates at random locations in maize chromosomes when introduced into maize cells by *Agrobacterium* mediated transformation. Selection for transformed maize cells is provided by the constitutively expressed AAD1 selectable marker gene in the T-DNA. In one embodiment, the artificial transposon, carrying tandem copies of the SCBV activator element, can be excised from its position in the original integration site (donor site), and can re-insert into other chromosomal loci (acceptor sites). The introduction of the potent SCBV transcriptional enhancer elements into acceptor sites adjacent to native maize genes causes aberrant expression of those nearby genes, thereby, in some instances, providing new identifiable traits to plants regenerated from the transformed tissues. Modern molecular biology methods are available which facilitate the isolation and identification of the affected genes near the acceptor site, thus providing the isolated genes for further exploitation.

Excision and mobilization of the artificial transposon from a donor integration site is mediated by the TnpA and TpnD proteins provided by an Spm transposase gene also located within the T-DNA of plasmid pEPS3004 (FIG. 1), and positioned outside of the artificial transposon TIR elements. To monitor when the artificial transposon leaves the donor site of integration, the C1/BP marker system provides a screenable visual marker which is inactive until the artificial transposon is precisely excised from the donor site. When the artificial transposon is excised, the nonfunctional BP gene is repaired and the screenable marker phenotype (red pigmentation in seed aleurones) can be easily detected. Such seeds may be selected and germinated, and the resultant plants may be characterized for any new desirable traits, such as, for example, drought tolerance, enhanced yield, etc. that arise due to aberrant expression of genes nearby the acceptor site.

An exemplary activation tagging DNA construct pEPS3004 has a nucleic acid sequence as set forth by SEQ ID NO: 1 and comprises the various elements described above. This construct is provided as an example and is not intended to be limiting. For example, additional activation tagging DNA constructs are contemplated by the present disclosure. For example, additional or alternative transposons, transcriptional enhancers, promoters, selectable and/or screenable markers can be used to form an activation tagging construct in accordance with the teachings herein, including those contemplated by one of ordinary skill in the art and as described below. Further it is contemplated that the elements may be varied as desired depending upon the use of the construct with methods known to those of ordinary skill in the art. Further, proper construct formation can also be confirmed by using methods known to those of ordinary skill in the art including, but not limited to, restriction digests and sequencing.

i. Coding Sequence for a Transposase

The disclosed construct includes a coding sequence for a transposase. A transposase is an enzyme that binds to the ends of a transposon and catalyzes the movement of the transposon to another part of the genome by a cut and paste mechanism or a replicative transposition mechanism. Exemplary transposases are known to those of ordinary skill in the art and include, but are not limited to, Ac, Ds, Mu, Spm, TAM1 and TAG transposases. In one particular example, a coding sequence for a transposase is the equivalent of the complement of the sequence comprising the coding sequences of TpnA and TpnD of a maize Spm transposase, as disclosed by bases 400 to 8045 of GenBank Accession No. M25427.1 (locus MZETNENSPM) (Pereira et al., *EBMO J*. 5: 835-841, 1986 which is hereby incorporated by reference in its entirety). For example, a coding sequence for a transposase corresponds to nucleic acids 483 to 8132 of SEQ ID NO: 1.

ii. Detectable Reporter Encoding Region

The disclosed activation tagging DNA construct comprises a detectable reporter encoding region to monitor transposition. In one embodiment, a detectable reporter encoding region comprises at least one sequence encoding a regulatory/reporter gene operably linked to a promoter.

a) Reporter Genes

Reporter genes are genes that are typically not present in the recipient organism or tissue and typically encode for proteins resulting in some phenotypic change or enzymatic property. Examples of such genes are provided in Weising et al., 1988. Recognized reporter genes include the β-glucuronidase (GUS) of the uidA locus of *E. coli*, the chloramphenicol acetyl transferase gene from Tn9 of *E. coli*, the green fluorescent protein from the bioluminescent jellyfish *Aequorea victoria* (and the myriad engineered derivatives thereof), green fluorescent protein from other animals (e.g., *Rinella*, or *Ptilosarcus*; see U.S. Pat. No. 7,528,242), and the luciferase genes from firefly *Photinus pyralis* (and the myriad engineered derivatives thereof). An assay for detecting reporter gene expression may then be performed at a suitable time after said gene has been introduced into recipient cells. In some instances a reporter gene may be used with or without a selectable marker.

In one embodiment, a detectable reporter encoding region comprises a sequence encoding anthocyanin regulatory gene B-Peru operably linked to a high level constitutive promoter and a sequence encoding anthocyanin regulatory gene C1 operably linked to a promoter, such as a high level constitutive promoter. In other examples, anthocyanin regulatory gene expression is used as a phenotypic marker, such as described by Shen and Petolino (*Mol. Breeding*, DOI 10.1007/s11032-006-9018-1, 2006) and in International Patent Publication No. WO 91/02059 (each of which is hereby incorporated by reference in its entirety). Shen and Petolino (*Mol. Breeding*, DOI 10.1007/s11032-006-9018-1, 2006) employ a globulin promoter which is expressed in the aleurone and embryo of maize seeds. In some examples, transcriptional activators of anthocyanin biosynthesis are operatively linked to a suitable promoter in an expression cassette and are used as non-phytotoxic markers for plant cell transformation.

At least two classes of regulatory genes, R1/B1 and C1/P11 control the anthocyanin biosynthetic pathway. Both of these two classes of regulatory genes are required for developmental and tissue specific pigmentation of plant and seed tissues in maize. The R1/B1 family encodes functionally exchangeable proteins with sequence homology to the basic helix-loop-helix (bHLH) DNA binding/dimerization domain found in the myC oncoproteins. The C1/P11 family encodes proteins with sequence homology to the DNA-binding domains of the myB-related oncoproteins. Anthocyanin pigment production involves at least 20 structural gene loci. C1 is involved in anthocyanin synthesis in seed tissue, such as the aleurone, the scutellum and the embryo axis, whereas P11 is involved in pigmentation of several tissues of the plant body and of the pericarp. B-Peru (Bp), an allele of B1, can substitute for R1 function in aleurone tissue.

In some examples, a B-Peru/C1 vector construct is used to indicate plant cell transformation (as described herein and in Shen and Petolino, Mol. Breeding, DOI 10.1007/s11032-006-9018-1, 2006). Commercially grown field corn genotypes typically include recessive alleles for the R1/B1 and C1/P11 regulatory genes such that under normal conditions their seed is non-pigmented even though they contain dominant alleles of the structural genes in the pathway. Constructing transformation vectors that comprise B-Peru and C1 genes under the control of seed-specific promoters in combination with genes of interest under the control of their own appropriate regulatory elements provides for the co-segregation of the visual marker and the trait; thereby creating the ability to easily identify transgenic segregates.

In an example, anthocyanin regulatory genes B-Peru and C1 are employed as screenable markers. These genes induce expression of anthocyanin biosynthetic genes when expressed ectopically. For example, to screen for kernels in which a transposition event occurred, B-Peru and C1 are expressed using a maize promoter, such as the maize globulin 1 promoter (a promoter that is expressed in aleurone tissues of the seed). In a particular example, the non-autonomous transposon is cloned in the 5' UTR region of the gene encoding B-Peru. This insertion prevents expression of the B-Peru protein and anthocyanins do not accumulate in the aleurone. However, when the transposon excises, the B-Peru gene is restored to a functional form and results in anthocyanin accumulation in aleurone tissues.

b) Promoters

A promoter typically includes at least an RNA polymerase binding site together with one or more transcription factor binding sites which modulate transcription in response to occupation by transcription factors. Numerous promoters useful for heterologous gene expression are available. A plant promoter is a native or non-native promoter that is functional in plant cells. Plant promoter regulatory elements include but are not limited to ribulose-1,6-bisphosphate (RUBP) carboxylase small subunit (ssu), β-conglycinin promoter, β-phaseolin promoter, ADH promoter, heat-shock promoters, and tissue specific promoters. In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter; see U.S. Pat. No. 6,166,302) and the like may be used. In one example, a promoter is a constitutive promoter. Exemplary constitutive promoters include, but are not limited to, the raspberry E4 promoter (U.S. Pat. Nos. 5,783,393 and 5,783,394), the multimerized 35S CaMV (Jones et al, *Transgenic Res.* 1: 285-297, 1992), the CsVMV promoter (Verdaguer et al., *Plant Mol. Biol.* 37: 1055-1067, 1998) and the melon actin promoter. Under certain circumstances it may be desirable to use an inducible promoter, which is responsible for expression of genes in response to a specific signal, such as: physical stimulus (heat shock genes), light (RUBP carboxylase), hormone (Em), metabolites, chemical (tetracycline responsive), and stress. In additional embodiments, tissue specific promoters which are responsible for gene expression in specific cell or tissue types, such as the leaves or seeds (e.g., zein, oleosin, napin, ACP, globulin and the like) may also be used. For example, tissue-specific promoters include the tomato E4 and E8 promoters (U.S. Pat. No. 5,859,330), the tomato 2AII gene promoter (Van Haaren et al., *Plant Mol. Bio.* 21: 625-640, 1993) and globulin 1 promoter which is expressed in aleurone and embryo tissues. Promoter regulatory elements may also be active (or inactive) during a certain stage of the plant's development as well as active in plant tissues and organs. Examples of such include but are not limited to pollen-specific, embryo-specific, corn-silk-specific, cotton-fiber-specific, root-specific, seed-endosperm-specific, or vegetative phase-specific promoter regulatory elements and the like.

iii. Non-autonomous Transposable T-DNA Cassette

An exemplary transposable T-DNA cassette includes a pair of DNA substrates for the transposase, having disposed therebetween a transcriptional enhancer; and, optionally a sequence encoding a selectable or screenable marker operably linked to the transcriptional enhancer. In one embodiment, a non-autonomous transposable T-DNA cassette is inserted into the detectable reporter encoding region such that the B-Peru and C1 genes express anthocyanins in a cell containing the maize activation tagging DNA construct only upon excision of the transposable cassette.

a. DNA Substrates for Transposase

Transposons, alternatively referred to as transposable elements, are naturally mobile pieces of DNA which are substrates for a transposase. Exemplary transposons such as Ac, Ds, Mu, Spm, TAM1 and TAG1 are elements that can insert themselves into genes and cause mutations. The mutations may be unstable due to subsequent excision of the transposon from the mutant locus during plant or seed development. (See, e.g., Doring, H. P. and Starlinger *Ann. Rev. Genet.* 20: 175-200, 1986; Federoff, N. "Maize Transposable Elements" in Mobile DNA. Wowe, M. M. and Berg, D. E., eds., *Amer. Soc. Microbiol.*, Wash., D.C., pp. 377-411, 1989.) An exemplary transposon-tagging strategy used to identify a semi-dominant mutation affecting plant height, hypocotyl elongation, and fertility has been described (see Wilson K et al., *Plant Cell* 8(4): 659-671, 1996). Transposon sequences may be incorporated into an activation tagging nucleic acid construct in order to move an enhancer around the plant genome. In one particular example of the disclosed activation tagging DNA construct, the transposon is a defective transposon (e.g., a transposon that lacks the enzyme functions to produce a DNA copy of itself and to integrate into a new chromosome position), such as a defective Spm transposon including an enhancer element (such as 4×SCBV) and selectable marker (such as AAD1). For example, the defective Spm transposon includes 4×SCBV enhancers and AAD1 as a selectable marker. In one particular example, the defective Spm transposon has a nucleic acid sequence corresponding to nucleic acids 13986 and 20163 of SEQ ID NO: 1.

b. Transcriptional Enhancer Elements

The disclosed platform includes an enhancer element which is useful in enhancing the transcription efficiency which may result in enhanced transcription of DNA sequences under control of the enhancer. Of particular interest is enhanced transcription of inserted gene sequences which may be of the same genetic origin as the host or of foreign origin, either the naturally occurring sequences (in both sense and antisense orientations) or synthetically prepared sequences. The enhancer element facilitates activation tagging.

A natural enhancer comprises a DNA sequence which in its native environment is upstream from and within about 600 bp of a promoter. Taking the initial nucleotide of the mRNA as 0, the sequence containing an enhancer in various embodiments is from about −50 to about −1000 bp, usually from about −50 to −950 bp, generally comprising about −100 to −800 bp. An enhancer domain is cis-acting and desirably is located within about 10,000 bp, usually about 2000 bp, more usually adjacent to or within about 1000 bp of a transcription initiation sequence to be enhanced. The enhancer may be in either orientation with respect to the transcription initiation sequence and can be located upstream or downstream in relation to the promoter it enhances, though it is usually upstream.

An enhancer domain of the present disclosure finds use with a wide variety of initiation sequences, including promoters that are naturally found under the control of the enhancer, e.g., in a cis position (adjacent and homologous) as well as those not normally associated with the particular enhancer (e.g., heterologous). The enhancer domain and transcription initiation domain may be from the same or different kingdom, family or species. Species of interest include prokaryotes and eukaryotes, such as bacteria, plants, insects, mammals, etc. Combinations include the described SCBV (viral) enhancer domain(s) with a transcription initiation region of a structural gene of: a host for SCBV (e.g., from sugarcane), another plant species (e.g., of the same or a different family), an insect, a vertebrate animal, a bacterium, a fungus, and so forth.

An exemplary transcriptional enhancer element comprises a plurality of copies of a previously unrecognized natural SCBV enhancer domain (the sequence of which is provided in SEQ ID NO: 2). For example, the enhancer element comprises at least two copies of the enhancer domain sequence, in some embodiments three or four or more copies, arranged in tandem. In one example, the transcriptional enhancer element consists of four copies of the SCBV (4×SCBV) enhancer. Other exemplary enhancer elements include, but are not limited to, the multimerized (4×) CaMV 35S enhancer, which is contained in the pSKI015 vector. Additional suitable enhancers include transcriptional enhancers from other caulimoviruses, such as the figwort mosaic virus (FMV), and peanut chlorotic streak caulimovirus, (PC1SV). It has been found that tandem repeats of the enhancer regions of FMV, PC1SV and MMV increase the expression of associated genes several-fold over single copies of the enhancer (Dey and Maiti, *Plant Mol. Biol.* 40: 771, 1999; Maiti and Shepherd, *Biochem. Biophys. Res. Commun.* 244: 440, 1998; Maiti et al., *Transgenic Res* 6: 142-156, 1997). In one example, the transcriptional enhancer element consists of four copies of the MMV (4×MMV) enhancer. In one example, the transcriptional enhancer element is comprised of at least one two different enhancer sequences, such as at least one SCBV enhancer sequence and at least one MMV enhancer sequence. Maiti et al., 1997, describes an FMV sequence with strong promoter activity, which corresponds to positions 6691 to 7003 of the complete FMV genome sequence found at GenBank Accession No. X06166. The promoter for the full-length transcript (FLt) of PC1SV is described in U.S. Pat. No. 5,850,019 and in Maiti et al., 1998, and corresponds to positions 5852 to 6101 of the complete genome sequence of PC1SV (found at GenBank Accession No. U13988). MMV is a double-stranded DNA plant pararetrovirus belonging to the caulimovirus family. The complete genome sequence of MMV is unpublished. The sequence of the characterized MMV promoter fragment has been described by Dey et al., 1999. The fragment with the highest promoter activity extends from nucleotides −297 to +63 from the transcriptional start.

In a particular embodiment, the enhancer (such as a 4×SCBV enhancer) and selectable marker (such as AAD1) are position in between the terminal inverted repeats (TIRs) of the transposable element (such as a Spm transposable element) within the disclosed construct. This is a non-autonomous transposon that requires a transposase in order to "hop". The transposase (such as a Spm transposase) is located on the same transformation vector but outside the TIRs of the transposon so that when the transposon is mobilized it will likely move to a location that not closely linked with the transposase (see FIG. 1).

c. Selectable or Screenable Marker

A disclosed activation tagging construct used to transform a plant normally contains at least one marker gene to facilitate selection of transformants (e.g., plants or plant cells bearing genomic insertions of the insertional mutagen) and which encodes a selectable or screenable marker for use in plant cells. A selectable marker confers a trait that one can select for by chemical means, e.g., through the use of a selective agent (e.g., an herbicide, antibiotic, or the like). A screenable marker confers a trait identified through observation or testing. Numerous suitable marker genes known in the art may be employed in practicing the disclosure.

A variety of selectable markers can be used, if desired. Exemplary selectable markers include but are not limited to antibiotic resistance genes, such as, kanamycin (nptII), G418, bleomycin, hygromycin, chloramphenicol, ampicillin, tetracycline, or the like, as well as those genes which encode for resistance or tolerance to and the like. Other examples of plant selectable markers that can provide resistance or tolerance to various herbicides include glufosinate (PAT), glyphosate (EPSPS), imazethyapyr (AHAS), hygromycin, methotrexate, phosphinothricin (bialaphos or glufosinate), imidazolinones, sulfonylureas and triazolopyrimidine herbicides, such as chlorsulfuron; bromoxynil, dalapon and many others. In one particular example, AAD1 serves as the plant transformation marker. Preference for a particular marker is at the discretion of the artisan, but any of the listed selectable markers may be used along with any other gene not listed herein which could function as a selectable marker.

The individually employed marker should accordingly permit the selection of transformed cells rather than cells that do not contain the inserted DNA.

In one example, the methods of the disclosure are carried out using a vector which includes the bar gene from *Streptomyces*, which encodes phosphinothricin acetyl transferase (PAT), that inactivates the active ingredient in the herbicide bialaphos, phosphinothricin (PPT). PPT inhibits glutamine synthetase, causing rapid accumulation of ammonia and cell death. Transgenic plants containing this gene exhibit tolerance to the herbicide, "BASTA". This gene can also be used as a selectable marker gene, since explants carrying the bar gene are capable of growing on selective media containing phosphinothricin (PPT), which is an active component of bialaphos.

In further embodiments, the methods of the disclosure are carried out using a vector which includes an herbicide resistance gene, conferring resistance to glyphosate-containing herbicides. Glyphosate refers to N-phosphonomethyl glycine, in either its acidic or anionic forms. Herbicides containing this active ingredient include "ROUNDUP" and "GLEAN". Exemplary genes for imparting glyphosate resistance include an EPSP synthase gene (5-enolpyruvyl-3-phosphosshikimate synthase).

The selection of an appropriate promoter effective to express the selectable marker-encoding sequence and the termination element for the selectable marker-encoding sequence may be accomplished by the use of well known, and/or commercially available sequences.

iv. Additional Elements

Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, osmotin UTR sequences, the maize streak virus coat protein leader sequence, as well as others available to a skilled artisan.

V. Plant Transformation

Myriad diverse techniques exist for introducing foreign recombinant vectors into plant cells, and for obtaining plants that stably maintain (at least, stable but for transposition as described herein) and express the introduced gene(s). Specifically contemplated transformation techniques include transformation with T-DNA using *Agrobacterium tumefaciens* or *Agrobacterium rhizogenes* as transformation agent, fusion, injection, biolistics (microparticle bombardment), silicon carbide whiskers, aerosol beaming, PEG, or electroporation as well as other possible methods. Such techniques include the introduction of genetic material coated onto microparticles directly into cells (U.S. Pat. No. 4,945,050 to Cornell and U.S. Pat. No. 5,141,131 to DowElanco, now Dow AgroSciences, LLC). In addition, plants may be transformed using *Agrobacterium* technology, see U.S. Pat. No. 5,177,010 to University of Toledo; U.S. Pat. No. 5,104,310 to Texas A&M; European Patent Application 0131624B1; European Patent Applications 120516, 159418B1 and 176,112 to Schilperoot; U.S. Pat. Nos. 5,149,645, 5,469,976, 5,464,763 and 4,940,838 and 4,693,976 to Schilperoot; European Patent Applications 116718, 290799, 320500, all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Syngenta; U.S. Pat. Nos. 5,463,174 and 4,762,785, both to Calgene; and U.S. Pat. Nos. 5,004,863 and 5,159,135, both to Agracetus. Other transformation technology includes whiskers technology (see U.S. Pat. Nos. 5,302,523 and 5,464,765, both to Zeneca, now Syngenta). Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plants can be transformed with a viral vector using the methods described in U.S. Pat. No. 5,569,597 to Mycogen Plant Science and Ciba-Geigy (now Syngenta), as well as U.S. Pat. Nos. 5,589,367 and 5,316,931, both to Biosource, now Large Scale Biology. The manner in which the DNA construct is introduced into the plant host is not critical.

For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation.

Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical. The Ti or Ri plasmid containing the T-DNA for recombination may be capable or incapable of causing gall formation, and is not critical so long as the vir genes are present in said host.

If Agrobacteria are used for the transformation, the DNA to be inserted is cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *A. tumefaciens* by means of a helper plasmid (conjugation).

Binary vectors can replicate themselves both in *E. coli* and in *Agrobacterium*. They comprise a selection marker gene and a linker or polylinker which are framed by the right and left T-DNA border regions. They can be transformed directly into *Agrobacterium* (Holsters et al., *Mol. Gen. Genet.* 163: 335-338, 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can be cultivated advantageously with

*A. tumefaciens* or *A. rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

For transformation of plant cells using *Agrobacterium*, explants may be combined and incubated with the transformed *Agrobacterium* for sufficient time to allow transformation thereof. After transformation, the *Agrobacterium* are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations, or for analysis of transposon excision as described herein. Regardless of transformation technique, gene(s) encoding protein(s) to be expressed in the plant are preferably incorporated into a gene transfer vector adapted to express said gene(s) in a plant cell by including in the vector plant promoter regulatory element(s), as well as 3' non-translated transcriptional termination regions such as Nos and the like; specific example are described herein.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In addition to numerous technologies for transforming plants, the type of tissue that is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein. The transformed plants may be analyzed for the presence of the gene(s) of interest and the expression level and/or profile conferred by the activation tagging system described herein. Numerous methods are available to those of ordinary skill in the art for the analysis of transformed plants. For example, methods for plant analysis include Southern and northern blot analysis, PCR-based (or other nucleic acid amplification-based) approaches, biochemical analyses, phenotypic screening methods, field evaluations, and immunodiagnostic assays (e.g., for the detection, localization, and/or quantification of proteins).

VI. Uses of the Transformed Plants

The tagged population, including plants transformed with the disclosed activating tagged platform, can be used to screen for particular phenotypes, such as agronomically important traits, mutations or a combination thereof. The insertion sites of the transposon can be determined by performing flanking sequence tag analysis. These sequences can be mapped to the genome using bioinformatics tools. Once the insertion sites are known and mapped, lines can be identified with insertions in or near specific genes. This population can be used for reverse genetic analysis to investigate phenotypes associated with activation tags near specific genes.

i. Screening for Agronomically Important Traits

The tagged populations can be used to screen for agronomically important traits by forward genetic screening assays. For example, the tagged population can be screened for phenotypes that provide beneficial traits to plants such as but not limited to drought tolerance, improved nitrogen use efficiency, increased seed oil content or altered starch content or other desired traits. Screening the population for other phenotypes such as altered plant development, morphology or metabolite accumulation may lead to improvements in the basic understanding of plant biology. Screens of this type are well known in the art and have been described in publications such as Bruce et al. (*J. Exper. Botany*, 53: 13-25, 2002), Agrama et al. (*Molecular Breeding* 5: 187-195, 1999), Baye et al. (*J. Cereal Science* 43: 236-243, 2006), Knutson and Grove (*Cereal Chern.* 71: 469-471, 1994), Guillaumie et al. (*Plant Physiol.* 143: 339-363, 2007), and Yamasaki et al. (*Plant Cell* 17: 2859-2872, 2005); each of these references is hereby incorporated by reference in its entirety.

In some embodiments, more than one screen is performed. For example, the primary screen is followed by a secondary screen of seed from events displaying the phenotypes. The secondary screen uses seed from the same generation screened in the primary screen but may include a larger number of plants than the primary screen.

Once the phenotype has been confirmed in the secondary screen, the phenotype is tested for genetic linkage with the tag insertion by screening the progeny of a cross between the non-transformed parental line and the tag line. When plants containing the tag element display the phenotype (such as increased drought tolerance) and plants that do not contain the tag element do not, the phenotype is considered to be genetically linked with the insert and likely to be caused by the tag element. To identify genes whose expression may be affected by such element, the location of the activation tagged element within the genome can be determined.

The genomic location of the tagged element can be determined by methods known to those of ordinary skill in the art. In one example, the genomic location of the tag element (such as ZeaTAG, a maize-based activation tagging element) is determined by isolating genomic sequences flanking the ZeaTAG element and comparing these sequences to the genomic sequence of maize. Sequences flanking the ZeaTAG element can be determined by a number of molecular biological techniques, including but not limited to, inverse PCR (iPCR) (Ochman et al., *Genetics*, 120: 621-6231988), TAIL (Liu et al., *Plant Journal* 8: 457-463, 1995) and ligation-mediated PCR (LMPCR) Prod'hom et al., *FEMS Microbiol Lett.* 158: 75-81, 1998). These sequences are compared to genomic sequences by sequence alignment tools such as the Basic Local Alignment Search Tool BLAST® to identify the location of the ZeaTAG element within the genome.

Genes flaking or interrupted by the ZeaTAG element are determined by examining the annotated genome. Transcription of genes flanking the ZeaTAG element may be responsible for the mutant phenotype. These genes may be overexpressed in wild-type maize to test whether they can confer a similar phenotype. To test this, the genes are cloned into transformation vectors driven by strong promoters or by their own promoter with enhancer sequences flanking them to enhance transcription. These vectors are introduced into wild-type maize by transformation and plants resulting from this transformation are tested for the phenotype.

Similarly, genes interrupted by the ZeaTAG element may cause the phenotype. To confirm that a gene interrupted by the element is responsible for the phenotype, expression of the gene can be disrupted and plants containing this disruption can be tested for the phenotype. The disruption of expression of specific genes can be accomplished by a number of methods know to those skilled in the art including but not limited to antisense RNA, artificial micro RNAs and identifying mutations in the gene by TILLING.

ii. Screening for Mutations

The tagged population can also be used for identifying mutations, such as by use of reverse genetic screening. Reverse genetic screening is looking for mutations affecting specific genes and subsequently testing the identified line for a mutant phenotype. The tagged population (such as a ZeaTAG population) can be used in reverse genetic analyses in several ways including but not limited to generating a collection Flanking Sequence Tags for the population (Jeong et al., *The Plant Journal* 45: 123-132, 2006) and generating an indexed collection of pooled samples of DNA from the tagged population (such as a ZeaTAG population) (May et al., *Molecular Biotechnology* 20: 209-221, 2002).

A collection of Flanking Sequence Tags can be generated by obtaining a sample from a plant, plant part or cell that has been "tagged" (such as by sampling leaf tissue from the ZeaTAG population), isolating DNA from each, identification of sequences flanking the insert and storing the sequences in a searchable database where the sequences are linked to the events from which they came. Plants containing insertions in or near genes that are hypothesized to cause a phenotype can be identified by searching the database. Plants containing these events can be tested for the phenotype.

An indexed collection of pooled samples of DNA from the tagged population can be generated and screened for tagged elements affecting expression of specific genes using strategies well known to those skilled in the art. These include, but are not limited to, isolating DNA from each plant within the population and arraying the DNA in microtiter plates. The DNA from each row and column within the plate can be pooled and aliquots of these pools can be pooled together. The pooled DNA from each plate can be pooled into larger pools. Insertions of the tag element (such as the ZeaTAG element) at genomic locations can be tested for using PCR with one primer specific for the genomic location and the other primer specific for the tag element (such as the ZeaTAG element). The pooled DNA samples are first screened by PCR and identified by amplification of a specific PCR product containing sequence from both the genomic location being interrogated and the tag element (such as the ZeaTAG element). The pools of DNA can be deconvoluted by first screening DNA from pools of microtiter plates, then to a specific microtiter plate and then to a specific well within the microtiter plate. Once identified, plants containing the tag element (such as the ZeaTAG element) can be screened for a specific phenotype using methods well known to those skilled in the art.

The following Examples illustrate methods used to produce plasmids and plants useful for practicing the subject invention. It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting the invention to the particular features or embodiments described.

Example 1

Transient Expression Testing of C1 and B-Peru Proteins for Induction of Anthocyanin Production in Immature Maize B104 Embryos This example demonstrates that expressing maize genes encoding C1 and B-Peru proteins together in maize B104 embryos results in induction of anthocyanin production.

It is well known in the field of maize genetics and maize gene expression that the C1 protein and the B-Peru (BP) protein coordinate to induce expression of genes that control the synthesis and accumulation of red anthocyanin pigments (Christensen et al., *Plant Mol. Biol.* 18: 675-689, 1992). Thus, in appropriate maize genetic backgrounds, co-expression of the C1 protein coding region and the BP protein coding region is revealed by pigment production.

In control experiments, the C1 coding region and the BP coding region were individually cloned to place them under the expression control of a maize ubiquitin1 promoter, which is constitutively active in most maize cell and tissue types. A 953 bp maize C1 coding region and a 1921 bp BP coding region were separately cloned between a 1991 bp maize Ubi1 promoter and a 254 bp nopaline synthase transcription terminator in plasmid pBluescript SK+ (Stratagene, La Jolla, Calif.) (see Table 1 for descriptions of components and their respective positions in SEQ ID NO: 1). In another pBluescript background plasmid, both the C1 and BP coding regions were cloned under the transcriptional regulation of a 1249 bp maize globulin1 gene promoter (Belanger and Kriz, *Genetics* 129: 863-872, 1991). Bulk preparations of plasmid DNAs were prepared using QiAfilter™ Plasmid Maxi Kits (Qiagen) and quantity and quality were analyzed using standard molecular methods.

Preparation of Maize B104 Embryos for Bombardment

Maize ears were collected 13 days after pollination (DAP) and surface sterilized with 50% bleach for 15 minutes, followed by five washes with sterile distilled water. Embryos were isolated using sterile forceps and 30 embryos were placed on a Petri plate containing MS medium (Murashige and Skoog, *Physiol. Plant.* 15: 473-497, 1962) with 3% sucrose for 24 hours in darkness at 28° C. On the day of bombardment, the embryos were moved to MS medium containing 12% sucrose and incubated in darkness at 28° for 4 hours prior to bombardment.

Preparation of Gold Particles with Plasmid DNAs and Bombardment Assay

Gold particles (1 μm diameter) were washed with 70% ethanol for 10 minutes, then three times with sterile water. The particles were dispensed in 50% glycerol at a concentration of 120 mg/mL. To 50 μL (6 mg) of gold particles, 5 μg of plasmid DNA, 50 μL of 2.5M $CaCl_2$ and 20 μL 0.1M spermidine were added. The reaction (total volume 125 μL) was incubated at room temperature for 10 min with gentle shaking, then for another 10 minutes without shaking. The DNA coated-gold particles were briefly centrifuged, washed with 150 μL of 70% ethanol and then with 100% ethanol. The final pellet was resuspended in 30 μL of 100% ethanol and subjected to a brief sonication with a Branson 3510 sonicator. A 10 μL aliquot of the gold-particles coated with DNA was spread on macrocarriers (BioRad, Hercules, Calif.) and used in bombardment assays using a BioRad PDS1000/He system. The embryos were transformed at a target distance of 6 cm using 1100 psi disks. Following bombardment, the embryos were moved to MS medium containing 3% sucrose and incubated under light (approximately 50 µEm$^{-2}$s$^{-1}$) for 48 hours at 28°. Accumulation of anthocyanin pigments was observed under a light microscope.

Transient Expression of C1 and BP Proteins

When maize B104 embryos were individually transiently transformed with plasmid DNAs carrying the maize C1 or BP coding regions controlled by the constitutive Ubi1 promoter, no red pigmentation was seen. In contrast, when the two genes were co-transformed into maize embryos, anthocyanin production was observed in about half of the embryos, attesting to the functionality of the C1 and BP proteins produced from the respective coding regions employed in this work, and proving the requirement that both proteins need to be present to induce pigment formation.

In other constructs, the C1 and BP protein coding regions were under the transcriptional control of a maize globulin1 gene promoter, which in maize is preferably functional in embryo and aleurone tissues (Belanger and Kriz, *Genetics* 129: 863-872, 1991). In control studies, when the C1 protein coding region and the BP coding region, both under the transcriptional control of a maize globulin1 gene promoter, were individually transiently transformed into maize B104 embryos, no red pigmentation was seen. Co-transformation of both genes produced B104 embryos exhibiting red pigmentation.

These studies demonstrated that both the Ubi1 promoter and the globulin1 promoter are able to drive expression of the C1 and BP anthocyanin regulatory genes in 13 DAP B104 immature embryos.

Example 2

Plasmids for Activation Tagging in Maize

This example describes the construction of a representative example activation tagging DNA construct (pEPS3004) for use in activating tagging in maize.

Generation of *Agrobacterium* Superbinary Plasmids

The superbinary system is a specialized example of an *Agrobacterium* shuttle vector/homologous recombination system (reviewed by Komari et al., *Meth. Mol. Biol.* 343: 15-41, 2006, Komori et al., *Plant Physiol.* 114: 1155-1160, 2007; see also European Patent No. EP604662B1 and U.S. Pat. No. 7,060,876). The *Agrobacterium tumefaciens* host strain employed with the superbinary system is LBA4404 (pSB1). Strain LBA4404(pSB1) harbors two independently-replicating plasmids, pAL4404 and pSB1. pAL4404 is a Ti-plasmid-derived helper plasmid which contains an intact set of vir genes (from Ti plasmid pTiACH5), but which has no T-DNA region (and thus no T-DNA left and right border repeat sequences). Plasmid pSB1 supplies an additional partial set of vir genes derived from pTiBo542. One example of a shuttle vector used in the superbinary system is pSB11, which contains a cloning polylinker that serves as an introduction site for genes destined for plant cell transformation, flanked by right and left T-DNA border repeat regions. Shuttle vector pSB11 is not capable of independent replication in *Agrobacterium*, but is stably maintained therein as a co-integrant plasmid when integrated into pSB1 by means of homologous recombination between common sequences present on pSB1 and pSB11. Thus, the fully modified T-DNA region introduced into LBA4404(pSB1) on a modified pSB11 vector is productively acted upon and transferred into plant cells by Vir proteins derived from two different *Agrobacterium* Ti plasmid sources (pTiACH5 and pTiBo542). The superbinary system has proven to be particularly useful in transformation of monocot plant species (See Hiei et al., *Plant J.* 6: 271-282, 1994, and Ishida et al., *Nat. Biotechnol.* 14: 745-750, 1996).

A representative transformation plasmid for production of activation tagged maize plants is pEPS3004, which has a pSB11 vector backbone (Japan Tobacco, see European Patent No. EP604662B1 and U.S. Pat. No. 7,060,876). The structure of pEPS3004 was validated by restriction enzyme analysis and DNA sequence determination of selected regions of the construct. The DNA sequence of the portion of pEPS3004 relevant to this work is provided in SEQ ID NO: 1, and a structural map illustrating pertinent features is given in FIG. 1. The descriptions of the elements in SEQ ID NO: 1 are presented in Table 1. SEQ ID NO: 1 illustrates one embodiment, but one skilled in the fields of plant molecular biology and plant gene expression will understand that certain other promoters, coding regions, transcription activator or terminator sequences, and the like may be substituted for analogous elements of SEQ ID NO: 1, and such other variations of SEQ ID NO: 1 are considered to be within the scope of this disclosure.

TABLE 1

Elements within SEQ ID NO: 1.

| Bases of SEQ ID NO: 1 | Description |
| --- | --- |
| 1 to 25 | T-DNA Right Border Repeat sequence as provided by the pSB11 vector. |
| 118 to 482 | Maize (*Zea mays*) Per5 transcription terminator region as disclosed in U.S. Pat. No. 6,699,984. |
| 491 to 8132 | Essentially the complement of the sequence comprising the coding sequences of TpnA and TpnD of a maize Spm transposase as disclosed by bases 400 to 8045 of GenBank Accession No. M25427.1\|MZETNENSPM. |
| 8137 to 10127 | Essentially the complement of the maize ubiquitin1 promoter and associated intron 1 as disclosed in U.S. Pat. No. U.S. Pat. No. 5,510,474 and bases 7 to 1990 of GenBank Accession No. S94464.1. |
| 10169 to 11417 | Promoter region of a maize globulin gene (essentially bases 2 to 1401 as disclosed in GenBank Accession No. L22344.1) |
| 11422 to 12374 | Encompasses a maize C1 protein coding sequence, which comprises bases 11440 to 12261, (essentially as disclosed in GenBank Accession No. AF320614) |

TABLE 1-continued

Elements within SEQ ID NO: 1.

| Bases of SEQ ID NO: 1 | Description |
|---|---|
| 12390 to 12643 | Nopaline synthase transcription terminator region as disclosed in bases 1847 to 2103 of GenBank Accession No. V00087.1. |
| 12703 to 13951 | Promoter region of a maize globulin gene (essentially bases 2 to 1401 as disclosed in GenBank Accession No. L22344.1) |
| 13982 to 14251 | En-I 5' terminal inverted repeat as disclosed by bases 1 to 270 of GenBank Accession No. M25427.1|MZETNENSPM |
| 15020 to 15301 | SCBV promoter activator element copy #1 |
| 15314 to 15595 | SCBV promoter activator element copy #2 |
| 15608 to 15889 | SCBV promoter activator element copy #3 |
| 15902 to 16183 | SCBV promoter activator element copy #4 |
| 16272 to 17668 | Rice (*Oryza sativa*) actin promoter with associated intron 1 and 5' UTR (essentially as disclosed as bases 12 to 1411 of GenBank Accession No. EU155408.1) |
| 17671 to 18561 | Coding sequence for AAD-1 herbicide tolerance gene as disclosed in US Patent Application No. 20090093366 |
| 18588 to 18944 | 3' Transcription terminator sequence from maize lipase gene essentially as disclosed as bases 921 to 1277 of GenBank Accession No. gb|L35913.1|MZELIPASE and in U.S. Pat. No. 7,179,902- |
| 19520 to 20160 | En-I 3' terminal inverted repeat as disclosed by bases 7647 to 8287 of GenBank Accession No. M25427.1|MZETNENSPM |
| 20191 to 22109 | Encompasses a maize B-Peru (BP) protein coding sequence, which comprises bases 20214 to 21905, (essentially bases 121 to 1970 of GenBank Accession No. X57276.1|) |
| 22125 to 22378 | Nopaline synthase transcription terminator region as disclosed in bases 1847 to 2103 of GenBank Accession No. V00087.1. |
| 22497 to 22521 | T-DNA Left border repeat sequence as provided by the pSB11 vector. |

Plasmid pEPS3004 was introduced into *Agrobacterium tumefaciens* strain LBA4404(pSB1) by procedures as previously taught (Komari et al., *Meth. Mol. Biol.* 343: 15-41, 2006, Komori et al., *Plant Physiol.* 114: 1155-1160, 2007; European Patent No. EP604662B1 and U.S. Pat. No. 7,060, 876), and the structure of the pSB1::pEPS3004 co-integrate plasmid was validated by restriction enzyme digestion of isolated plasmid DNA by standard methods.

Example 3

*Agrobacterium*-Mediated Transformation of Maize

This example describes representative methods for transforming maize cells, and production of plants and seeds from such transformed cells.

Immature Embryo Production

Seeds from a B104 inbred were planted into 4-gallon-pots containing Sunshine Custom Blend® 160 (Sun Gro Horticulture, Bellevue, Wash.). The plants were grown in a greenhouse using a combination of high pressure sodium and metal halide lamps with a 16:8 hour Light:Dark photoperiod. To obtain immature embryos for transformation, controlled sib-pollinations were performed. Immature embryos were isolated at 10 to 13 days after pollination when embryos were approximately 1.4 to 2.0 mm in size.

Infection and Co-Cultivation

Prior to embryo excision and transformation, maize ears were surface sterilized by immersing them in 50% commercial bleach with Tween 20 (1 or 2 drops per 500 mL) for 10 minutes and triple-rinsed with sterile water. A suspension of *Agrobacterium* cells containing a superbinary vector was prepared by transferring 1 or 2 loops of bacteria grown on YEP (5 g/L yeast extract, 10 g/L peptone, 5 g/L sodium chloride, 15 g/L Bacto Agar) solid medium containing 50 mg/L Spectinomycin, 10 mg/L Rifampicin, and 50 mg/L Streptomycin at 28° for 3 days or 25° for 4 days into 5 mL of liquid infection medium (MS salts, ISU Modified MS Vitamin stock (1000×, 2 g/L glycine, 0.5 g/L each of thiamine HCl and pyridoxine HCl, 0.05 g/L nicotinic acid as provided in Che et al. (*Plant Cell Reports*, 25: 1024-1034, 2006), 3.3 mg/L Dicamba, 68.4 gm/L sucrose, 36 gm/L glucose, 700 mg/L L-proline, pH 5.2) containing 100 µM acetosyringone. The solution was gently pipetted up and down using a sterile 5 mL pipette until a uniform suspension was achieved, and the concentration was adjusted to an optical density of 0.3 to 0.5 at 600 nm ($OD_{600}$) using an Ultrospec 10 Cell Density Meter (GE Healthcare/Amersham Biosciences, Piscataway, N.J.). Immature embryos were isolated directly into a micro centrifuge tube containing 2 mL of the infection medium. The medium was removed and replaced twice with 1 to 2 mL of fresh infection medium, then removed and replaced with 1.5 mL of the *Agrobacterium* solution. The *Agrobacterium* and embryo solution was incubated for 5 minutes at room temperature and then transferred to co-cultivation medium, which contained MS salts, ISU Modified MS Vitamins, 3.3 mg/L Dicamba, 30 gm/L sucrose, 700 mg/L L-proline, 100 mg/L myo-inositol, 100 mg/L Casein Enzymatic Hydrolysate, 15 mg/L $AgNO_3$, 100 µM acetosyringone, and 2.3 to 3 gm/L Gelzan™ (Sigma-Aldrich, St. Louis, Mo.), at pH 5.8. Co-cultivation incubation was for 3 to 4 days at 25° under either dark or 24-hour white fluorescent light conditions (approximately 50 $\mu Em^{-2}s^{-1}$).

Resting and Selection

After co-cultivation, the embryos were transferred to a non-selection MS-based resting medium containing MS salts, ISU Modified MS Vitamins, 3.3 mg/L Dicamba, 30 gm/L sucrose, 700 mg/L L-proline, 100 mg/L myo-inositol, 100 mg/L Casein Enzymatic Hydrolysate, 15 mg/L $AgNO_3$, 0.5 gm/L MES (2-(N-morpholino)ethanesulfonic acid monohydrate; Fischer Scientific, Waltham, Mass.), 250 mg/L Carbenicillin, and 2.3 gm/L Gelzan™, at pH 5.8. Incubation was continued for 7 days at 28° under either dark or 24-hour white fluorescent light conditions (approximately 50 $\mu Em^{-2}s^{-1}$). Following the 7 day resting period, the embryos were transferred to selective medium. For selection of maize tissues transformed with a superbinary plasmid containing a plant expressible AAD1 selectable marker gene, the MS-based resting medium (above) was used supplemented with Haloxyfop. The embryos were first transferred to selection media containing 100 nM Haloxyfop and incubated for 1 to 2 weeks, and then transferred to selection media containing 500 nM Haloxyfop and incubated for an additional 2 to 4 weeks. Transformed isolates were obtained over the course of approximately 5 to 8 weeks at 28° under either dark or 24-hour white fluorescent light conditions (approximately 50 $\mu Em^{-2}s^{-1}$).

Those skilled in the art of maize transformation will understand that other methods of selection of transformed plants are available when other plant expressible selectable marker genes (e.g., other herbicide tolerance genes) are used.

Pre-Regeneration

Following the selection process, cultures exposed to the 24-hour light regime were transferred to an MS-based pre-regeneration medium containing MS salts, ISU Modified MS Vitamins, 45 gm/L sucrose, 350 mg/L L-proline, 100 mg/L myo-inositol, 50 mg/L Casein Enzymatic Hydrolysate, 1 mg/L AgNO$_3$, 0.25 gm/L MES, 0.5 mg/L naphthaleneacetic acid, 2.5 mg/L abscisic acid, 1 mg/L 6-benzylaminopurine, 250 mg/L Carbenicillin, 2.5 gm/L Gelzan™, and 500 nM Haloxyfop, at pH 5.8. Incubation was continued for 7 days at 28° under 24-hour white fluorescent light conditions (approximately 50 $\mu Em^{-2}s^{-1}$).

Regeneration and Plantlet Isolation

For regeneration, the cultures were transferred to an MS-based primary regeneration medium containing MS salts, ISU Modified MS Vitamins, 60 gm/L sucrose, 100 mg/L myo-inositol, 125 mg/L Carbenicillin, 2.5 gm/L Gelzan™, and 500 nM Haloxyfop, at pH 5.8. After 2 weeks at 28° under either dark or 24-hour white fluorescent light conditions (approximately 50 $\mu Em^{-2}s^{-1}$), tissues were transferred to an MS-based secondary regeneration medium composed of MS salts, ISU Modified MS Vitamins, 30 gm/L sucrose, 100 mg/L myo-inositol, 3 gm/L Gelzan™, at pH 5.8, with, or without, 500 nM Haloxyfop. Regeneration/selection was continued for 2 weeks at 28° under either 16-hour or 24-hour white fluorescent light conditions (approximately 50 $\mu Em^{-2}s^{-1}$). When plantlets reached 3 to 5 cm in length, they were excised and transferred to secondary regeneration medium (as above, but without Haloxyfop) and incubated at 25° under 16-hour white fluorescent light conditions (approximately 50 $\mu Em^{-2}s^{-1}$) to allow for further growth and development of the shoot and roots.

Seed Production

Plants were transplanted into Metro-Mix® 360 soilless growing medium (Sun Gro Horticulture) and hardened-off in a growth room. Plants were then transplanted into Sunshine Custom Blend 160 soil mixture and grown to flowering in the greenhouse. Controlled pollinations for seed production were conducted.

Example 4

Identification of Maize Plants Having Transpositions of the Tandem SCBV Activator Element This example describes analyses of maize cells into which an activation tagging construct (exemplified by pEPS3004, described above) had been integrated, analysis of plants derived therefrom, and characterization of these cells and plants after excision of the non-autonomous transposable T-DNA cassette from within the activation tagging construct.

In control studies, the C1 coding region and the BP coding region were individually cloned to place them under the control of a maize ubiquitin) promoter, which is constitutively active in most maize cell and tissue types. When the C1 or BP genes thus constructed were individually transiently transformed into maize B104 embryos, no red pigmentation was seen. In contrast, when the two genes were co-transformed into maize embryos anthocyanin production was observed, attesting to the functionality of the C1 and BP proteins produced from the respective coding regions employed in this work, and proving the requirement that both proteins need to be present to induce pigment formation.

As present in the T-DNA of pEPS3004 (FIG. 1 and SEQ ID NO: 1), the C1 protein coding region is under the transcriptional control of a maize globulin gene promoter, which in maize is active in cells comprising the aleurone layer of the seeds. In control studies, when the C1 protein coding region and the BP coding region, both under the transcriptional control of a maize globulin gene promoter, were individually transiently transformed into maize B104 embryos, no red pigmentation was seen. Co-transformation of both genes produced B104 embryos exhibiting red pigmentation, attesting to the functionality of the globulin promoter employed in this work to direct seed-specific expression.

As present in the T-DNA of pEPS3004, the BP coding region is downstream (in the transcriptional sense) from a copy of the maize globulin promoter, but is displaced from it by 6177 bases of intervening DNA. These intervening bases prevent the transcription of a functional mRNA encoding the BP protein, initiated by the globulin promoter. Thus, in order for the BP protein to be produced under the control of the second copy of the globulin promoter, these intervening bases must be removed in such a fashion that results in creation of an active gene (e.g., by appropriate juxtaposition of the globulin promoter and BP coding region).

The intervening bases comprise part of an artificial transposon partially derived from elements of the maize Enhancer or Suppressor-mutator (En/Spm) transposon. In the native En/Spm transposon system, transposase proteins TpnA and TpnD encoded by Spm act on 5' and 3' Terminal Inverted Repeat (TIR) sequences to mobilize the transposon via excision from a donor chromosomal locus and insertion into distal locations. The 6177 bp of the intervening bases separating the globulin promoter and BP coding region include the 5' and 3' TIR sequences that flank an active gene encoding a plant selectable marker protein (AAD1), under the expression control of a (constitutive) rice actin promoter (FIG. 1). Thus, the artificial transposon of the subject invention comprises a pair of TIR elements which flank a plant selectable marker gene. An additional feature of the artificial transposon of the subject invention is the inclusion of four tandem copies of a transcriptional activator element (SEQ ID NO: 2) derived from a promoter found in the genome of Sugar Cane Bacilliform Virus (SCBV), positioned between the 5' TIR element and the rice actin promoter that controls expression of the AAD1 gene (see FIG. 1).

The T-DNA of pEPS3004 as disclosed in SEQ ID NO: 1 and FIG. 1 integrates at random locations in maize chromosomes when introduced into maize cells by *Agrobacterium* mediated transformation. Selection for transformed maize cells is provided by the constitutively expressed AAD1 selectable marker gene in the T-DNA. It is a feature of the subject disclosure that the artificial transposon, carrying tandem copies of the SCBV activator element, can be excised from its position in the original integration site (donor site), and can re-insert into other chromosomal loci (acceptor sites). The introduction of the potent SCBV transcriptional enhancer elements into acceptor sites adjacent to native maize genes causes aberrant expression of those nearby genes, thus providing new identifiable traits to plants regenerated from the transformed tissues. Modern molecular biology methods are available which facilitate the isolation and identification of the affected genes near the acceptor site, thus providing the isolated genes for further exploitation.

Excision and mobilization of the artificial transposon from a donor integration site is mediated by the TnpA and TpnD proteins provided by an Spm transposase gene also located within the T-DNA of plasmid pEPS3004 (FIG. 1), and positioned outside of the artificial transposon TIR elements. To monitor when the artificial transposon leaves the donor site of integration, the C1/BP marker system provides a screenable marker which is inactive until the artificial transposon is precisely excised from the donor site. When the transposon is excised, the nonfunctional BP gene is repaired and the screenable marker phenotype (red pigmentation in seed aleurones) can be easily detected. Such seeds may be germinated and the resultant plants characterized for any new desirable traits, such as, for example, drought tolerance, enhanced yield or a combination thereof.

Validation of artificial transposon excision and the ability of C1 and B-Peru genes to report such excision was obtained in maize B104 embryos transformed with LBA4404(pSB1) carrying the pEPS3004 vector (an "Spm-ZeaTAG vector"). The transformed embryos were analyzed for the synthesis and accumulation of anthocyanin pigments as a consequence of the excision. Three of 250 embryos showed anthocyanin accumulation in the first experiment, and 7 of 250 embryos showed anthocyanin accumulation in the second experiment. Molecular evidence for artificial transposon excision was obtained from genomic DNA isolated from the embryogenic callus tissue that accumulated anthocyanin. Polymerase Chain reaction (PCR), using opposing primers corresponding to the DNA sequence flanking the artificial transposon unit of the vector was performed using the genomic DNA as template to confirm the empty donor site DNA sequence. The PCR reactions produced amplicons of about 247 bp, the expected size if the artificial transposon had been appropriately excised. The forward primer (5'-GTACCTCTTCCTGGAGCACCAG-3' SEQ ID NO: 10) is located between the 13961 bp and 13982 bp and the reverse primer (5'-TGTAGAACCCGTCCGTCCGTC-CACGTCAG-3' SEQ ID NO: 11) is located between the 20359 bp and 20383 bp within SEQ ID NO: 1.

PCR products were cloned into a TOPO vector (Invitrogen, Carlsbad, Calif.) and transformed into *E. coli* cells. Plasmid DNA was prepared from 47 isolated colonies and sequenced. Sequencing of the PCR product demonstrated that Spm-dependent excision of the artificial transposon (corresponding to positions 13982-20160 of SEQ ID NO: 1) occurred in maize B104 embryos transformed with the pEPS3004 Spm-ZeaTAG vector. A sample of the determined sequences is presented in Table 2. A clear dominance of the sequence represented by Empty DS 2 was found.

TABLE 2

Sequence of 47 empty donor sites (EDS) after transposition of artificial transposon.

| | | |
|---|---|---|
| pEPS3004 DS | cagtgt{artificial transposon}acgagaca (SEQ ID NO: 3) | |
| Empty DS 1 (2, 2) | cagtgt----------------------acgagaca (SEQ ID NO: 4) | |
| Empty DS 2 (18, 21) | cagtgt-----------------------.cgagaca (SEQ ID NO: 5) | |
| Empty DS 3 (1, 0) | cagtgt-----------------------.cgagacg (SEQ ID NO: 6) | |
| Empty DS 4 (1, 0) | cagtgt-----------------------.tgagaca (SEQ ID NO: 7) | |
| Empty DS 5 (1, 0) | cagcgt-----------------------.cgagaca (SEQ ID NO: 8) | |
| Empty DS 6 (0, 1) | cagtg.-----------------------...agaca (SEQ ID NO: 9) | |

In Table 2, numbers in parentheses indicate number of clones having the indicated sequence in the first and second studies. The dots and double underlined bases indicate base pair deletions and transitions, respectively, in the EDS sites. See also FIGS. 3A-3C.

The pEPS3004 Spm-ZeaTAG vector was also used to produce stably transformed maize plants. These plants produced kernels with different seed phenotypes, as a consequence of different spatial and temporal excisions of the artificial transposon. Those familiar with the biology of maize seed development will understand that if the artificial transposon is excised from the donor site at a time early in seed development, prior to the meiosis that gives rise to the ovule (e.g., germinal transposition), the entire aleurone layer will accumulate anthocyanins, giving a relatively uniform red/purple color to an entire seed. In contrast, if the artificial transposon is excised after pollination and while the aleurone layer is developing (e.g., somatic transposition), sectors of the aleurone will accumulate anthocyanins (FIG. 2A and FIG. 2B). Only germinal transpositions will result in transposon-modified loci in the plant's germ line cells, and these, and not somatic transposition events, will be transmitted to subsequent generations. FIG. 2A and FIG. 2B show transgenic B104 seeds that accumulated anthocyanins in the seed aleurones due to excisions of the artificial transposon at various stages of seed and embryo development.

Example 5

Method of Producing Activation Tagged Plants

This example describes how a maize activation tagging construct such as pEPS3004 (described above) can be integrated into a plant (e.g., maize) genome in order to produce activation tagged plants.

Figure 4:
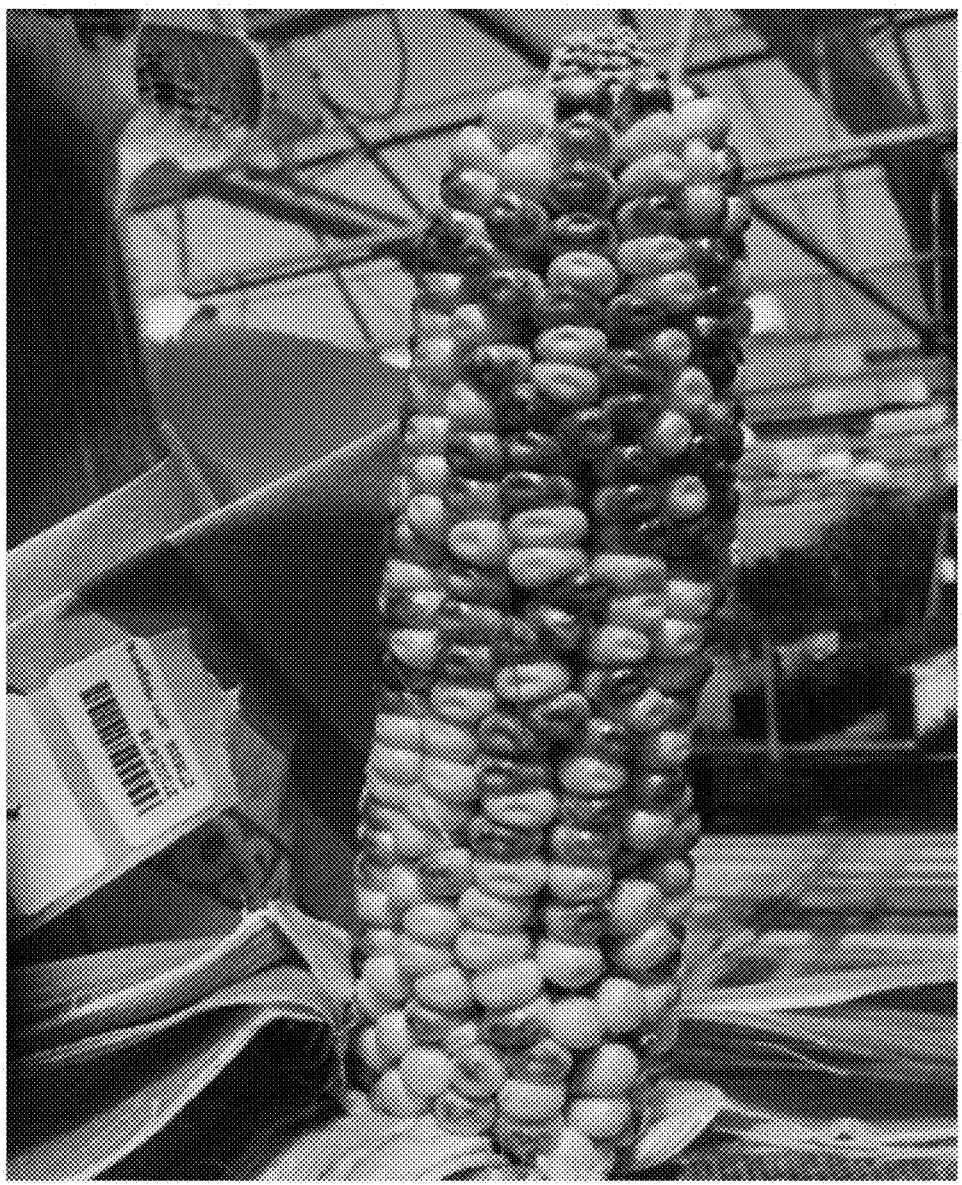
FIG. 4 is a photograph of an ear of corn displaying germinal transposition of the ZeaTAG element from pEPS3004. Germinal transposition generates purple maize kernels resulting from transposition prior to aleurone development.

The phenotype of the $BC_1$ ear (a cross between T0 plant B104) provided genetic evidence of transposition. $BC_1$ ears with all yellow seed indicated that no transposition of the transposon had occurred (FIG. 4), while $BC_1$ ears with yellow and purple kernels indicated that germinal transposition has occurred and $BC_1$ ears with yellow and purple-spotted seed to yellow seed indicated that somatic transposition had occurred. $BC_1$ ears with combination of yellow, purple and purple spotted seed indicated that both germinal and somatic transposition has occurred in vivo. Analysis of the genetic cross between 271 T0 B104 plants with wild-type B104 pollen revealed four kinds of excision/transposition phenotypes as shown in the Table 3.

TABLE 3

BC$_1$ (T0 B104 plant × Wild-type B104) ear phenotypes
Transposition category

|  | No Excision (100% yellow) | Germinal (Purple to yellow) | Somatic (Purple-spotted to Yellow) | Germinal + Somatic |
|---|---|---|---|---|
| Number of BC$_1$ ears | 135 | 27 | 73 | 36 |

These genetic tests confirmed the results of biochemical and molecular analyses of the transposon excision in B104 transgenic plants regenerated from embryo transformations using the Spm-ZeaTAG vector.

To evaluate whether the transposon remained active in the BC$_1$ generation and to increase the amount of seed containing active transposons, approximately 5000 BC$_1$ kernels from 68 events showing somatic transpositions (yellow seed with purple spots) were planted in the field in Molokai, Hi. Approximately 95% of the seeds germinated and seedlings were sprayed with Assure II (the AAD1 herbicide resistance gene provides resistance to Assure II containing quizalofop) to remove any non-transgenic seedlings that may have been in the population. As expected, no seedlings were sensitive to Assure II. The plants were allowed to grow to maturity and backcrossed to B104 to generate BC$_2$ seed. Ears were harvested from approximately 4000 plants from 67 events. Kernels from these ears were characterized for seed phenotypes as before. The phenotypes are tabulated in Table 4; see also FIG. 5.

TABLE 4

BC$_2$ (BC$_1$ B104 plant × Wild-type B104) ear phenotypes
Transposition category

|  | No Excision (100% yellow) | Germinal (Purple to yellow) | Somatic (Purple-spotted to Yellow) | Germinal + Somatic |
|---|---|---|---|---|
| Number of BC$_2$ ears | 10 | 18 | 2881 | 1017 |

These results indicate that the transposon is actively transposing, in either somatic or germinal tissues, in the 99.7% of BC$_1$ generation plants and that germinal excision is occurring in 26.3% of the plants. Furthermore, 44% of the events showed a germinal excision frequency of at least 30% (e.g. at least 30% of the plants from that event produced ears with at least one purple kernel).

The purple kernels from plants displaying a germinal excision event were screened to determine whether they contain the transposon. If integration of an excised transposon occurs at a site that is not genetically linked to the site where the construct originally inserted, ~50% of the purple seed will contain the herbicide resistance gene. Two hundred purple kernels from 20 events (10 plants from each of 20 events) were planted in the greenhouse. These plants were sprayed with Assure II to select plants containing the herbicide resistance gene. Eighty-five percent (85%) of the events (17 events) contained segregation ratios consistent with a 1:1 segregation ratio (Chi square test ≥0.05) of resistant to susceptible plants consistent with the hypothesis that these contain the transposable element containing the herbicide resistance gene at a location unlinked to the location of the transformation integration site (containing the anthocyanin marker genes). One event segregated 8 resistant to 1 susceptible (1 did not germinate) suggesting that the transposable element integrated at a site linked with the transformation integration site. The other two events segregated 0 resistant to 10 susceptible and 1 resistant to 9 susceptible, suggesting that the selectable marker may have integrated in an unfavorable site in these events or that the resistance marker has been silenced.

These genetic tests confirmed the results of biochemical and molecular analyses of the transposon excision in B104 transgenic plants regenerated from embryo transformations using the Spm-ZeaTAG vector and that the transposon in the Spm-ZeaTAG vector is transposing from the original site of integration and integrating into a genetically unlinked position in the maize genome.

Example 6

Forward Genetic Screening of the ZeaTAG Population

This example describes forward genetic screening of the ZeaTAG population for altered phenotypes.

Drought Stress Screens

To identify ZeaTAG lines that contain mutations conferring drought tolerance, plants from individual ZeaTAG events are planted in a field. Water is withheld to cause drought stress during the reproductive phase of the growth cycle; roughly 2 weeks prior to flowering to approximately 2 weeks after flowering. The target is to achieve 4 weeks of stress period at flowering stage. Environmental modeling is used to predict accurate corn evapotranspiration demand based on soil moisture monitoring and weather data (air temperature, vapor pressure deficit, wind speed, and net radiation). Plants are monitored for drought symptoms such as leaf rolling by visual observation, increased leaf temperature by infrared thermometers, reduced photosynthesis by chlorophyll fluorescence and reduced yield by measuring grain production. Plants that show significantly less leaf rolling, lower leaf temperature, higher rates of photosynthesis or have significantly more yield under water stress conditions are identified and used in subsequent screens.

ZeaTAG events displaying significantly more drought tolerance are planted in a replicated field trial to confirm the drought tolerant phenotype. These events are planted in a randomize split block design with at least 3 replications. One block is irrigated with water sufficient to prevent water stress. The other block is grown under water deficient conditions as described above. Plants are monitored for leaf rolling, increased leaf temperature, decreased photosynthesis and decreased yield as described above. Plants with significantly less leaf rolling, lower leaf temperature, greater photosynthesis or greater yield than untransformed control plants are considered to have passed the secondary screen.

Nitrogen Use Efficiency Screens

To identify ZeaTAG events with greater nitrogen use efficiency than non-transgenic control plants a primary screen is performed. Plants containing approximately 40,000 ZeaTAG containing events are grown in the field under nitrogen deficient conditions. Plants are grown in fields with less than 35 lbs of N per acre. Plants are monitored for chlorosis by visual inspection, increased leaf temperature by infrared thermometers, and decreased yield by grain harvest. These parameters are compared with non-transgenic control plants. ZeaTAG lines showing less chlorosis, lower leaf temperature, higher photosynthetic rates or greater yields than non-transgenic control lines are evaluated in secondary screens.

As a secondary screen, ZeaTAG events displaying significantly more nitrogen use efficiency are planted in a replicated field trial to confirm the phenotype. These events are planted in a randomize split block design with at least 3 replications. One block is irrigated with sufficient nitrogen fertilizer to prevent nitrogen stress. The other block is grown under nitrogen deficient conditions as described above. Plants are monitored for chlorosis by visual inspection, increased leaf temperature by infrared thermometers, and decreased yield by grain harvest. Plants with significantly less chlorosis, lower leaf temperature, greater photosynthesis or greater yield than untransformed control plants are considered to have passed the secondary screen.

Once the phenotype has been confirmed in the secondary screen, the phenotype is tested for genetic linkage with the ZeaTAG insertion by screening the progeny of a cross between the non-transformed parental line and the ZeaTAG line. When plants containing the ZeaTAG element display the phenotype and plants that do not contain the ZeaTAG element do not, the phenotype is considered to be genetically linked with the insert and likely to be caused by the ZeaTAG element. To identify genes whose expression may be affected by the ZeaTAG element, the location of the ZeaTAG element within the genome is determined.

The genomic location of the ZeaTAG element is determined by isolating genomic sequences flanking the ZeaTAG element and comparing these sequences to the genomic sequence of maize. Sequences flanking the ZeaTAG element can be determined by a number of molecular biological techniques, including but not limited to, inverse PCR (iPCR) (Ochman et al., *Genetics*, 120: 621-6231988), TAIL (Liu et al., *Plant Journal* 8: 457-463, 1995) and ligation-mediated PCR (LMPCR) Prod'hom et al., *FEMS Microbiol Lett.* 158: 75-81, 1998). These sequences are compared to genomic sequences by sequence alignment tools such as BLAST® to identify the location of the ZeaTAG element within the genome.

Genes flaking or interrupted by the ZeaTAG element are determined by examining the annotated genome. Transcription of genes flanking the ZeaTAG element may be responsible for the mutant phenotype. These genes may be over-expressed in wild-type maize to test whether they can confer a similar phenotype. To test this, the genes are cloned into transformation vectors driven by strong promoters or by their own promoter with enhancer sequences flanking them to enhance transcription. These vectors are introduced into wild-type maize by transformation and plants resulting from this transformation are tested for the phenotype.

Similarly, genes interrupted by the ZeaTAG element may cause the phenotype. To confirm that a gene interrupted by the element is responsible for the phenotype, expression of the gene can be disrupted and plants containing this disruption can be tested for the phenotype. The disruption of expression of specific genes can be accomplished by a number of methods know to those skilled in the art including but not limited to antisense RNA, artificial micro RNAs and identifying mutations in the gene by TILLING.

Example 7

Reverse Genetic Screening of the ZeaTAG Population

This example describes reverse genetic screening of the ZeaTAG population for mutations.

Reverse genetic screening is looking for mutations affecting specific genes and subsequently testing the identified line for a mutant phenotype. The ZeaTAG population can be used in reverse genetic analyses in several ways including but not limited to generating a collection Flanking Sequence Tags for the population (Jeong et al., *The Plant Journal* 45: 123-132, 2006) and generating an indexed collection of pooled samples of DNA from the ZeaTAG population (May et al., *Mol Biotech.* 20: 209-221, 2002).

A collection of Flanking Sequence Tags is generated by sampling leaf tissue from the ZeaTAG population, isolating DNA from each, identification of sequences flanking the insert and storing the sequences in a searchable database where the sequences are linked to the events from which they came. Genomic DNA is isolated using the Qiagen DNAeasy® Plant Kit (Qiagen, Germantown, Md.) using the protocol recommended by the manufacturer. Sequences flanking the insert are identified using Ligation Mediated PCR (Mueller et al., *Science* 246: 780-786, 1989) as modified by Yephremov and Saedler (*Plant Journal* 21: 295-305, 2000). Briefly, genomic DNA from a ZeaTAG line is fragmented restriction enzyme digestion and denatured. A biotinylated oligonucleotide primer complementary to the sequence at the end of the ZeaTAG element is hybridized to the fragmented DNA and extended by DNA polymerase. Streptavidin coated magnetic beads are added to the mixture to bind DNA fragments containing DNA fragments extended from this primer. A double-stranded DNA adaptor of known sequence is ligated to the unknown end. These fragments are PCR amplified using oligonucleotides complementary to sequences within the ZeaTAG element and the DNA adaptor at the other end. The sequence of the PCR fragment is then determined and mapped to the maize genomic sequence by BLAST®. These sequences locate the site of insertion of the ZeaTAG element. Genes within a ~10 kbp may be up-regulated by the enhancer sequences within the ZeaTAG element.

Plants containing insertions in or near genes that are hypothesized to cause a phenotype can be identified by searching the database. Plants containing these events can be tested for the phenotype.

In view of the many possible embodiments to which the principles of the disclosed technologies may be applied, it will be recognized that the illustrated embodiments are only preferred examples of the invention and should not be taken as limiting its scope. Rather, the scope of the invention is defined by the following claims. We therefore claim as our invention all that comes within the scope and spirit of these claims.

We claim:

1. A method, comprising:
   randomly integrating an activation tagging construct into one or more maize plant chromosomes to thereby generate one or more tagged maize plants;
   screening the one or more tagged maize plants to identify one or more maize plants having a modified phenotype relative to an untagged maize plant lacking the activation tagging construct; and
   selecting the one or more tagged maize plants identified as having a modified phenotype, wherein the modified phenotype is an enhanced agronomic trait,
   wherein the activation tagging construct comprises at least one sugarcane bacilliform viral (SCBV) enhancer element set forth in SEQ ID NO: 2, and the enhancer element is operatively linked to a promoter that is native to the maize plant.

2. The method of claim 1, comprising generating a tagged population of maize plants.

3. The method of claim 1, further comprising identifying a tagged population of maize plants.

4. The method of claim 1, wherein the activation tagging construct comprises a selectable marker and the method further comprises selecting a tagged population of maize plants based on the presence of the selectable marker in the tagged population of maize plants.

5. The method of claim 1, wherein the activation tagging construct is randomly integrated by transformation.

6. The method of claim 5, wherein the activation tagging construct is randomly integrated by *Agrobacterium* mediated transformation.

7. The method of claim 1, wherein the activation tagging construct is randomly integrated by transposition.

8. The method of claim 1, wherein the activation tagging construct comprises at least two copies of the SCBV enhancer.

9. The method of claim 8, wherein the activation tagging construct comprises four copies of the SCBV enhancer.

10. The method of claim 1, wherein the activation tagging construct comprises the sequence of SEQ ID NO: 1.

11. The method of claim 1, wherein the enhanced agronomic trait comprises increased drought tolerance, increased nitrogen use efficiency, increased seed oil content, or increased yield under an environmental stress condition.

12. The method of claim 11, wherein the environmental stress condition comprises drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density.

* * * * *

SEQUENCE LISTING

```
<160> NUMBER OF SEQ ID NOS: 11

<210> SEQ ID NO 1
<211> LENGTH: 22521
<212> TYPE: DNA
<213> ORGANISM: Artificial Sequence
```

<220> FEATURE:
<223> OTHER INFORMATION: plasmid

<400> SEQUENCE: 1

```
gtttacccgc caatatatcc tgtcaaacac tgatagtttt taattaaggc gcgccatgcc     60
cgggcaagcg gccgctctag aactagtgga tctggccacc gtggcctagg ccggccgttg    120
gatatatgcc gtaacaattg ttatgttaca agcacagcg  ccgctgcaac actgataaat    180
gccaactgga atggtagatg aactcttcaa gaaacaggtg acatattcc  atgagtttat    240
tgagttgtga ttttggtttt tggagtcaaa acatcacagg tcaaataagc agatctatgg    300
caaccgaaga atgaacacat cttatacatt gagttattaa tagatacaca ttttacaatg    360
tgttaaataa aaccccaaag atcgatcata tgataaaatc acagccatgc ttacttattt    420
aaacaaaata cgccaccaac atcacaaaca attcagcaca tcaagcgact tcagtgccct    480
cagtttcgcg cacatcagta agctacctgg gcgcatataa gagtgtgggg gccgacactc    540
ttagtgaata attttttta atatccaatt ttattttct  ccctcccgg  atgggaagcc    600
tccataacag cacaatataa gcacaacatt caatatatca caacacaagc accatattca    660
acataacata acacaagcac catattcaat attcatacaa gttcaagtcc atacgaaaga    720
agttcaaatc catctaaaac aagttaaagt ccatacaaaa cgcaatcata gtaagttcca    780
cacaagcctc catattaatt cattctgttg gtgggtcatt ggagccgccg ccacttgtgt    840
tcatcaataa gtccataaac gtgctctgat ccggaggcgg actagcatga tgtgagcctg    900
aacccttta  aagaaacaaa catttgttag tttaccgagt aactaattaa acatatacat    960
agactgcaac atatacatgc atgttttcta gtaactgctt aaacaacgaa gcaaatagag   1020
atgcaaagga tatcaactta acgtactgat cctggtgagt gtgagggcaa tcctggtgat   1080
tgtgactgcc cacgaggagg aaatccccac ggcatcggcg gtggcatctg tgtttgcatc   1140
ggtggccaaa tgcctggctg gcgaggtgcc cacggcatca tttgccctcc tatcacaccc   1200
aatggcatca attggtcttg gacagaagtt gcagaaccct gaaacagaag acacactctt   1260
gtttatgatt aagaagttac ggtgatcaac aataaaagta actatagatc atgcgaatga   1320
caaaagttta aaatagatca tgtacaagca aacatgtaga aagacagaga gcaagcaacc   1380
aatgattatc agacaaatga tgtttagtag aggattgtac ctgtgatcca tctgccgctg   1440
cagtggagcg gtccgatgat tgtccagaca ccggatgtgt gatgataggg ggttgttgaa   1500
aaggcggcat gccgaactga gttccggcac ctccatacat ctgcaaatag attattcatc   1560
agttttcag  ttaatcggac ttgagaaaca acgaaataac aaaaaaatga tacctgatgt   1620
agcatccaat tttgcatttg ttgcatctgt tgctgcactt gttgcttata ttgcgccata   1680
ctctcctcca tctgagtcat cttctcaagc agctctcctt cacgtgcaga tggtcgtcgg   1740
ggtcgattcg acccagctga gaaattggac cgtctagtgt aactccgacg ggggacaaca   1800
ccgtcaccaa ttgctaacct gtaagagtat catatatata tatatatata tgtagtaaat   1860
gacaagacat gactaaacag taacaatgtg acaagcgcat atacctccca tgtggtacgc   1920
ctccaccagc cttataagcc gcctccgtat cgaactcacc agtgagccaa tccgtgtctg   1980
gaccattttt ttctctcacg ttgtcaatgt agcgagccta tgaaaaaatc atccaagtca   2040
caacaaaggc atatcatgtt catcttagag tcgatttca  tacttaccag tttctctgtc   2100
gcattactgt cattccagtat ttccggatga ttccggatcgg gacccttgtg tccctcgacg   2160
aagacttgaa gcaaagtagg ctccactcca tttcgagccg cctgcaacac atgattaaaa   2220
```

```
agtctagaca agtctatgca attaacaatt gaccaggcaa tttgacacat accatacgtg    2280
cagccttgcc aacgtgtcca tctgccccga agaagtggac ccctggcttg ctcaaccgat    2340
tcatacgatt tctattagat atggccaaga actcctcaga agcccaatac tcacacatcc    2400
acgcccaagc atccgaatgg tggctcaacc aatccacctc actctctttg tactgctgag    2460
ccgtcaggtg aatttccttt gccatattcg cgtcacaata gttcccctga cgcttttggt    2520
acaccgtgac ggccctcaat cgtgctttat acatcatacc ctttacagct ctatctgctg    2580
agccattgaa tacctcacgc acatatgaat catccaaggt atagggtcg cacacgcgaa     2640 attggccctg caaatttgaa gatcaccaga gacttacaaa tgcaaaatct gaattcaatt    2700
tgaatatcac aagggactta cccaaaacaa atcccacact ttgcttgtgt gtgtcccgtc    2760
gttcccgtac ggcttgagat cccaatgagc ccagtaatga gcagctatct cttgaccgcc    2820
ctctgtcacc atcgccgggt aggcgaatcg caaacaaatc cccaactctg tgaggattgg    2880
tgtgcgatgc cctgttccgt cccaactaac ctccttccac gccctggtgc ctttcggttc    2940
aataaccctc cgttgatcga agggtttaga aggcttcaat gtgagggacc gacgatacct    3000
acaaatgaaa gtttgttatt taacaaagaa aatcatttac ttaaaacttc aacttgacaa    3060
taaaacttca actcaacaat aagaatacct gatggcacgc cgtggcggag cctgtgtggc    3120
agcctcctct gtagaagcgt ctgctcccga agtctcctct ccatcgtcca gttctgcggc    3180
agcttcctca gcctccgcgt ccacagctgc ctccgcgtcc acagctgcct ccgcagtagg    3240
tgccatagta ggtgccacta aatcagctgc acgcgaagta gtcccttctg tattggaggg    3300
tccgctgcta ccccgcatct gctctaggga ggcaagcaac tgctcttgcc tgcttctgct    3360
tgttgtggtg ccctgaaatg taaacaattt tagattgcta gctggcccca gtaactaaac    3420
taagaaaaaa acaagtacct caaacatgtt aggagcacca ctggaacccc tcgaccttcg    3480
tgatctggat ctcctaccag acgaatccat cctgaacatc tgcaataatt cacaaaatag    3540
taagtatgta taaattttc acaaagtaat gcatattaaa taaacaaaaa caagagtgtg    3600
ccattacatc tacgaattat gtatcaaaaa tcgtcggcat cagagtcctc ttcggcgaca    3660
cgtgtattaa gttgttcaac ccattgttgt gtttcaagaa ctgtttcttc caacctttga    3720
cgttttgaat ttgatgaaat tggttcctcc attaactcta cggtaagaga agctaactca    3780
tttagtcctg ccccttcgga tacaatacta tcattgtcgc tatcgtctgc ttgatcaccg    3840
acttcttgga agacaacatc atcttcatca tcatcattgg tgcttaaatt gtagttttga    3900
tatcggtaag ggtgaacctc tggattaact ttatatgcaa cccaccaggt tttaaaactt    3960
ttatgaggat aactcaaata gtacacctga tgcgcttgat gtgccaggat gatattgttg    4020
tactcattgc ctttataccc tgatgcgtgc tttacctcca ccatcccgaa ttcatcaact    4080
cgtgtgccaa cttgtggatc aaaccatata caatcaaacg tcacaagtct caaaggtttg    4140
tgacctccaa atgtatactc ggttatgtct tgaacaatac cataatagtc ctccaattgt    4200
ccatcgtcgc tatacgaact tgctacaact ccgctgtttg ttgtagctgc aagtggacga    4260
ctcgcttcta gttttgctgt tcgaaaacgg tatccattaa tatcatagcg atcaaatttt    4320
cttgcggtca attgaccatg tgatatttgt agcaagtctt tggagacact ggcttcaggt    4380
ttcttacact acaaaaatga ggaacgaata aaaataaata ctatgtaaca tctgaactta    4440
agttcgaaaa aaagatgggc aaggaggaaa ttacatgctc gtggaaccac tgcacgaagg    4500
acgggccacc gtgtaaccct ttcagacgta ggtcatccaa ctgcttttga gtaagttgtt    4560
tgttgggttt atatatgcta tcaaagattt ggaaataagg atgaagttct ggcatattga    4620
```

```
catacaaaaa aagcagggtc ttgttacgct ctatcgttcc cacaagatgt gatgtgtaag      4680
ctccgacacc tttaccgtcc cacttaaaag cacttagatc agtgattgga gcttgctcgg      4740
caacatggta gcgtgtcgtt tgcgcattca cgttgtttgt gtctgaaaaa tacttgcttg      4800
agaataatgt gatctctctg gctgcgaacg cctctgcaat acaccsctca acccttgcct      4860
tattccgcac cattcctctg agtttttca attctctttc ttgactatac atccacctga       4920
actgtgcagg tcctcctacc aacgcttccc aaggtagatg cacaagcaaa tgttgcatac      4980
aattaaaaaa tccaggtggg aatacttttt ccatcttaca tacaaggaca acgatttcct      5040
tctcaaacct caacatcaat ttctttgaga tttccttagc acatatctgc ttataaaaat      5100
aactgagttc tgcaaatatc ttccacacat cgggactgaa gtatccacga aacattaccg      5160
gcactagcct ttcaatcaaa atgtgatagt catgactctt caacccaacg agtttaccag      5220
tgtcgaggtt aactgcccgt tttatattag ccgcatagcg atctgggaac ctcagctttt      5280
tcaaccattg aaatatctct tctcgctctt gccgtttcag acaataagga gcttgtggcc      5340
gactctcaga tccacttgga ttttttctaa gctcaaggtg cggacgatca caaagttcag      5400
ctaagtctct tcttgcattc atgttatctt tggtttgacc ggtgaagtcg aagcacatgc      5460
ttatgatgct ttccgcaaca ttacgttctt ggtgcatcaa atctatatta tgtggtaaca      5520
gcaatgcctt cgtataaggt agctcccaga taaacgagat gtgcgtccaa ttgtgttctt      5580
taccatcccc ttgaaatcga cctcctacac ccggttttag gtcacgatgt tgtctcatga      5640
tattttcacc agtttgtcgc ttcggtggcc catctctaac cctcttgcct tttcgaaatg      5700
actttgtatc ctttctaaaa ggatgattat agggaaggag cgtcggtga acatcaaaaa       5760 atgtttcctt cttaccatgt tctaacctat atgcttgtga gtcacccata catatcggac      5820
aacgcagtat gccgtggaca caccaaccag aaaaaatgcc atatgctagc agatcatgaa      5880
ttgaccatag atatgctgcg cgtagagtaa acaacatttt cagatgacta tcatatgcct      5940 caacccctg ccacaacatt tttagttctt cgatcaacgg ttccataaat acattgattt       6000
ttgttacagg gtccttcgga cctggaacaa taagggcaag aaacatgacc tcttctttca      6060
tgcatttgtt aggagggaga ttgtagggca tcataaaaac tggccaacat gagtaagaag      6120
tggaattatt ggagtaagga gtgaatccat ccgtcgacaa accaagacga acactcctag      6180
ggtctcttgc aaattctgga tcaaaacggt cgagagcctg ccaggcctcg ccatctgagg      6240
gatgcaccat gacatccgga tcttggccct gacgatcccc ttctttatgc cacctcattt      6300
gctttgctgt ctcttgattt agaaagagac gcttaagccg tggagtgata ggcatgtacc      6360
ggagttgctt gatcggcacc tttgtcgtaa cctcgtttcc atcctcatct agcaccactg      6420
catatcttga cttactgcag tggatgcaat gtgtggtatt ttcatgctcc ttccagaaca      6480
acatgcaatt gtcctcgcaa gcatcaatct tttggtagtt catgccaaga ccagctacga      6540
gcttcttgca atggtacaag tctttcggca tgttatgatt cggtgggctg atatcaataa      6600
tcagtttcac aatatcgttg taacatttgt tggagaaggt gtactttgac ttcatcgcca      6660
tgagacgtgt taccacctgc agtacgctca cattggttcc ttcatgcact ttagcctctg      6720
aggcttcaag aagcttgtag aactctctca catcctctgg aaaagcttga ttattctgta      6780
gatctgggta ctcattccta atatcatcca acatctcttc cattcggtct atatcctggt      6840
ccccatccga ttcaatagta tggtccacct ctccatgctc atgccatacc agatagtttg      6900
gcataaagcc atgtttgaaa atatgatacg agagctccac tttttttcaac cgaaccaagt     6960 tccgacattt tatacacggg cacctcgcta aacgagcatc accaacaaat gcgagtgcca      7020
```

```
cgaattcatc tgcaactctc aaccatgcat cagagtgacc atgagtgaca ctgtcgaatc     7080
catcgtacat cgcccttctt cgatcgtcac tcatattcaa agctaaaaaa acatataatt     7140
agtgtctatt aaataatttt gacatataat tagtgtctat tgatacatta tttatttatt     7200
taataatttt tgagctcatg caggaagttt ttatgcaaag caaccaaaca ataatgcttt     7260
tgggtatgca gcctagttcc catattttgt tttcttgaaa cttgaacaat aatgcttttg     7320
ggtatgcagg attcgttgaa cacaacagga caaaacgtta acaagtacta cacgtgatat     7380
gttttctatt ctaaaacata aaatcattgt ttttttggta taaacaatat aaatatctga     7440
ctactttgct catatcaaga tatatgccta gtctcatgac tggaccgggt caagatgtac     7500
gcgaaaatgt gtttggctgc aggaaaaaaa caccccaccat tttgctgtag tttttgcccc     7560
ctcccccccc ccctctctca aatcagcagt agcaacggct tttctcaggc tgagaacaga     7620
gttcttaagc ttgacataat gctagatcag tggcaatgcc actaaaaaca ttaagtcggc     7680
aattaatacc acatagcgtt ttgacttctt gagttctaga actggaacag ggcaacagg      7740 aacatgattt tgcacagaat gcaagcacct tttaccatta ttttcaatga aacaagcaca     7800
acagaaagtc agaaaccctg tactaaccat cattttcaat gaaacatgtc ttggctggac     7860
agtgttgtca tctcgtaatc aggtgcttgc atttcatcac aggaagagag tacaattcat     7920
ggacctgagg ttgggcagaa acattttgct tacgctaagt gaggctgccc gcccggcgtc     7980
tgcctcggct gcgaggtcgc ccgctggcag ggcgaggccg cccgcccgac gccgcccgcc     8040
cgaggccgcc tgccgcccgg cgtctggctt ggctgcgagg ccgcccgccg cctggctcgg     8100
ctcggccgcc cggcgctact tggaggtgcg cgcctgcaga agtaacacca acaacaggg      8160 tgagcatcga caaagaaac agtaccaagc aaataaatag cgtatgaagg cagggctaaa      8220
aaaatccaca tatagctgct gcatatgcca tcatccaagt atatcaagat cgaaataatt     8280
ataaaacata cttgttttatt ataatagata ggtactcaag gttagagcat atgaatagat    8340
gctgcatatg ccatcatgta tatgcatcag taaaacccac atcaacatgt atacctatcc     8400
tagatcgata tttccatcca tcttaaactc gtaactatga agatgtatga cacacacata     8460
cagttccaaa attaataaat acaccaggta gtttgaaaca gtattctact ccgatctaga     8520
acgaatgaac gaccgcccaa ccacaccaca tcatcacaac caagcgaaca aaaagcatct     8580
ctgtatatgc atcagtaaaa cccgcatcaa catgtatacc tatcctagat cgatatttcc     8640
atccatcatc ttcaattcgt aactatgaat atgtatggca cacacataca gatccaaaat     8700
taataaatcc accaggtagt ttgaaacaga attctactcc gatctagaac gaccgcccaa     8760
ccagaccaca tcatcacaac caagacaaaa aaaagcatga aagatgacc cgacaaacaa      8820 gtgcacggca tatattgaaa taaggaaaa gggcaaacca aaccctatgc aacgaaacaa      8880
aaaaaatcat gaaatcgatc ccgtctgcgg aacggctaga gccatcccag gattccccaa     8940
agagaaacac tggcaagtta gcaatcagaa cgtgtctgac gtacaggtcg catccgtgta     9000
cgaacgctag cagcacggat ctaacacaaa cacggatcta acacaaacat gaacagaagt     9060
agaactaccg ggccctaacc atgcatggac cggaacgccg atctagagaa ggtagagagg     9120
gggggggggg gggaggacga gcggcgtacc ttgaagcgga ggtgccgacg ggtggatttg     9180
ggggagatct ggttgtgtgt gtgtgcgctc cgaacaacac gaggttgggg aaagagggtg     9240
tggagggggt gtctatttat tacggcgggc gaggaaggga aagcgaagga gcggtgggaa     9300
aggaatcccc cgtagctgcc ggtgccgtga gaggaggagg aggccgcctg ccgtgccggc     9360
tcacgtctgc cgctccgcca cgcaatttct ggatgccgac agcggagcaa gtccaacggt     9420
```

```
ggagcggaac tctcgagagg ggtccagagg cagcgacaga gatgccgtgc cgtctgcttc    9480
gcttggcccg acgcgacgct gctggttcgc tggttggtgt ccgttagact cgtcgacggc    9540
gtttaacagg ctggcattat ctactcgaaa caagaaaaat gtttccttag ttttttttaat   9600 ttcttaaagg gtatttgttt aattttttagt cactttattt tattctattt tatatctaaa   9660 ctattaaaata aaaaaactaa aatagagttt tagttttctt aatttagagg ctaaaataga   9720
ataaaataga tgtactaaaa aaattagtct ataaaaacca ttaaccctaa accctaaatg    9780
gatgtactaa taaaatggat gaagtattat ataggtgaag ctatttgcaa aaaaaaagga   9840
gaacacatgc acactaaaaa gataaaactg tagagtcctg ttgtcaaaat actcaattgt    9900
cctttagacc atgtctaact gttcatttat atgattctct aaaacactga tattattgta    9960
gtactataga ttatattatt cgtagagtaa agtttaaata tatgtataaa gatagataaa   10020
ctgcacttca aacaagtgtg acaaaaaaaa tatgtggtaa tttttttataa cttagacatg   10080 caatgctcat tatctctaga gaggggcacg accgggtcac gctgcactgc aggtcgactc   10140
tagaggatcc ccccgcgccg atctagaaag cttgccgagt gccatccttg gacactcgat   10200
aaagtatatt ttatttttt tatttttgcca accaaacttt ttgtggtatg ttcctacact   10260
atgtagatct acatgtacca ttttggcaca attacaaaaa tgttttctat aactattaga   10320
tttagttcgt ttatttgaat ttcttcggaa aattcacata tgaactgcaa gtcactcgaa   10380
acatgaaaaa ccgtgcatgc aaaataaatg atatgcatgt tatctagcac aagttacgac   10440
cgatttcaga agcagaccag aatcttcaag caccatgctc actaaacatg accgtgaact   10500
tgttatccag ttgtttaaaa attgtataaa acacaaataa agtcagaaat taatgaaact   10560
tgtccacatg tcatgatatc atatatagag gttgtgataa aaatttgata ttgtttcggt   10620
aaagttgtga cgtactatgt gtagaaacct aagtgaccta cacataaaat catagagttt   10680
caatgtagtt cactcgacaa agactttgtc aagtgtccga taaaaagtat tcagcaaaga   10740
agccgttgtc gatttactgt tcgtcgagat ctctttgccg agtgtcacac taggcaaagt   10800
ctttacggag tgtttttcag gctttgacac tcggcaaagc gctcgattcc agtagtgaca   10860
gtaatttgca tcaaaaatag ccgagagatt taaaatgagt caactaatag accaactaat   10920
tattagctat tagtcgttag cttctttaat ctaagctaaa accaactaat agcttatttg   10980
ttgaattaca attagctcaa cggaattctc tgttttttct ataaaaaagg gaaactgccc   11040
ctcatttaca gcaaactgtc cgctgcctgt cgtccagata caatgaacgt acctagtagg   11100 aactcttttta cacgctcggt cgctcgccgc ggatcgagt cccaggaaca cgacaccact   11160
gtggaacacg acaaagtctg ctcagaggcg gccacaccct ggcgtgcacc gagccggagc   11220
ccggataagc acggtaagga gagtacggcg ggacgtggcg accgtgtgt ctgctgccac   11280 gcagccttcc tccacgtagc cgcgcggccg cgccacgtac cagggcccgg cgctggtata   11340
aatgcgcgcc acctccgctt tagttctgca tacagccaac ccaacacaca cccgagcata   11400
tcacagtgac actacaccat ggacgagaga gcgagcgcga tggggaggag ggcgtgttgc   11460
gcgaaggaag gcgttaagag aggggcgtgg acagcaagg aggacgatgc cttggccgcc   11520
tacgtcaagg cccatggcga aggcaaatgg agggaagtgc cccagaaagc cggtttgcgt   11580
cggtgcggca agagctgccg gctgcggtgg ctgaactacc tccggcccaa catcaggcgc   11640
ggcaacatct cctacgacga ggaggatctc atcatccgcc tccacaggct cctcggcaac   11700
aggtggtcgc tgattgcagg caggctgcct ggccgaacag acaatgaaat caagaactac   11760
tggaacagca cgctgggccg gagggcaggc gccggcgccg gcgccggcgg cagctgggtc   11820
```

```
gtcgtcgcgc cggacaccgg ctcgcacgcc accccggccg cgacgtcggg cgcctgcgag    11880
accggccaga atagcgccgc tcatcgcgcg gaccccgact cagccgggac gacgacgacc    11940
tcggcggcgg cggtgtgggc gcccaaggcc gtgcggtgca cgggcggact cttcttcttc    12000
caccgggaca cgacgccggc gcacgcgggc gagacggcga cgccaatggc cggtggaggt    12060
ggaggaggag gaggagaagc agggtcgtcg gacgactgca gctcggcggc gtcggtatcg    12120
cttcgcgtcg gaagccacga cgagccgtgc ttctccggcg acggtgacgg cgactggatg    12180
gacgacgtga gggccctggc gtcgtttctc gagtccgacg aggactggct ccgctgtcag    12240
acggccgggc agcttgcgta gacaacaagt acacgtatag atgtccaata agcacgaggc    12300
ccgcgagccc ggcacgaagc ccgcttttg ggcccggtcc gagcccggca cggcccggtt    12360
atatgcagac cccgagctcg aatttccccg atcgttcaaa catttggcaa taaagtttct    12420
taagattgaa tcctgttgcc ggtcttgcga tgattatcat ataatttctg ttgaattacg    12480
ttaagcatgt aataattaac atgtaatgca tgacgttatt tatgagatgg ttttttatga    12540
ttagagtccc gcaattatac atttaatacg cgatagaaaa caaatatag cgcgcaaact    12600 aggataaatt atcgcgcgcg gtgtcatcta tgttactaga tcgggaatta agcttatata    12660
ccgtcgacct cgaggcgcgc catgcccgc gccgatctag aaagcttgcc gagtgccatc    12720
cttggacact cgataaagta tattttattt tttttatttt gccaaccaaa cttttgtgg    12780 tatgttccta cactatgtag atctacatgt accattttgg cacaattaca aaatgtttt    12840 ctataactat tagatttagt tcgtttattt gaatttcttc ggaaaattca catatgaact    12900
gcaagtcact cgaaacatga aaaccgtgc atgcaaaata aatgatatgc atgttatcta    12960
gcacaagtta cgaccgattt cagaagcaga ccagaatctt caagcaccat gctcactaaa    13020
catgaccgtg aacttgttat ccagttgttt aaaaattgta taaacacaa ataaagtcag    13080 aaattaatga aacttgtcca catgtcatga tatcatatat agaggttgtg ataaaaattt    13140
gatattgttt cggtaaagtt gtgacgtact atgtgtagaa acctaagtga cctacacata    13200
aaatcataga gtttcaatgt agttcactcg acaaagactt tgtcaagtgt ccgataaaaa    13260
gtattcagca aagaagccgt tgtcgattta ctgttcgtcg agatctcttt gccgagtgtc    13320
acactaggca aagtctttac ggagtgtttt tcaggctttg cactcggca aagcgctcga    13380 ttccagtagt gacagtaatt tgcatcaaaa atagccgaga gatttaaaat gagtcaacta    13440
atagaccaac taattattag ctattagtcg ttagcttctt taatctaagc taaaaccaac    13500
taatagctta tttgttgaat tacaattagc tcaacggaat tctctgtttt ttctataaaa    13560
aagggaaact gcccctcatt tacagcaaac tgtccgctgc ctgtcgtcca gatacaatga    13620
acgtacctag taggaactct tttacacgct cggtcgctcg ccgcggatcg gagtcccagg    13680
aacacgacac cactgtggaa cacgacaaag tctgctcaga ggcggccaca ccctggcgtg    13740
caccgagccg gagcccggat aagcacggta aggagagtac ggcgggacgt ggcgacccgt    13800
gtgtctgctg ccacgcagcc ttcctccacg tagccgcgcg gccgcgccac gtaccagggc    13860
ccggcgctgg tataaatgcg cgccacctcc gctttagttc tgcatacagc caacccaaca    13920
cacacccgag catatcacag tgacactaca ccacaggtac ctcttcctgg agcaccagtg    13980
tcactacaag aaaacgtcaa aggagtgtca gttaattaaa gagtgtcggg gccgacactc    14040
ttaatcgaag taaagtgtg ggttttgctg caccgacact cttaatttaa gagtgtcggg    14100
gtcccgatga aaccgacgct tttaatttaa gagtgtgggt ttttccacac cgacactctt    14160
atgaatgtta ccctaaattc cccaatccta ttctacagcc gtcgtgcttc ttctctcctt    14220
```

```
tctccctgcc cgccgtccag tatacagtcg accgccaccg tctctccagt ctagccagcg   14280
gcgtgcggcc tcgccgagcc agcgtgggac gggcggccga gccaccagtg gcgggcgggc   14340
tcgccaagca gcgccgggcg ggcggcctcg ccaagcagag cgcgcacctc caagtagcgc   14400
cgggcggccg agccgagcca ggcggcgggc ggcctcgcag ccaagccaga cgccgggcgg   14460
caggcggcct cgggcgggcg gcgtcgggcg ggcggcctcg ccctgccagc gggcgacctc   14520
gcagccgagg cagacgccgg gcgggcagcc tcacttagcg taagcaaaat gtttctgccc   14580
aacctcaggt ccatgaattg tactctcttc ctgtgatgaa atgcaagcac ctgattacga   14640
gatgacaaca ctgtccagcc aagacatgtt tcattgaaaa tgatggttag tacagggttt   14700
ctgactttct gttgtgcttg tttcattgaa ataatggta aaaggtgctt gcattctgtg   14760
caaaatcatg ttcctgttgc ccctgttcca gttctagaac tcaagaagtc aaaacgctat   14820
gtggtattaa ttgccgactt aatgttttta gtggcattgc cactgatcta gcattatgtc   14880
aagcttaaga actctgttct cagcctgaga aaagccgttg ctactgctga tttgagagag   14940
gggggggggg aggggcaaa aactacagca aaatggtggg tgttttttc ctgcaggcgg   15000 ccgcttaatt aaattttaca caaagcatcg cataggatgc gcactcacac accgaaagtt   15060
gagatgcctt ctcagtgctt tcatgggtcc tccacgctcc atacgtcatt gcttacgatc   15120
tcctccactg gtcgtcattg cttacgtcag tgagatcgac tgcgtcttct gcgccttcga   15180
cgttgtcgcc cctgtgtgg cactcttctg cttctttatt cagccagtat gtaacatccc   15240
cccatggtct gaaatgatca tctgttggcc ttggcctgtc gatgacactc gaacggtgtt   15300
cggatccgag tacacaaagc atcgcatagg atgcgcactc acaccgaa agttgagatg   15360 ccttctcagt gctttcatgg gtcctccacg ctccatacgt cattgcttac gatctcctcc   15420
actggtcgtc attgcttacg tcagtgagat cgactgcgtc ttctgcgcct tcgacgttgt   15480
cgccccttgt gtggcactct tctgcttctt tattcagcca gtatgtaaca tcccccatg   15540 gtctgaaatg atcatctgtt ggccttggcc tgtcgatgac actcgaacgg tgttcggatc   15600
cgagtacaca aagcatcgca taggatgcgc actcacacac cgaaagttga tgccttct   15660 cagtgctttc atgggtcctc cacgctccat acgtcattgc ttacgatctc ctccactggt   15720
cgtcattgct tacgtcagtg agatcgactg cgtcttctgc gccttcgacg ttgtcgcccc   15780
ttgtgtggca ctcttctgct ctttattca gccagtatgt aacatccccc catggtctga   15840
aatgatcatc tgttggcctt ggcctgtcga tgacactcga acggtgttcg gatccgagta   15900
cacaaagcat cgcataggat gcgcactcac acccgaaag ttgagatgcc ttctcagtgc   15960
tttcatgggt cctccacgct ccatacgtca ttgcttacga tctcctccac tggtcgtcat   16020
tgcttacgtc agtgagatcg actgcgtctt ctgcgcctt cgacgttgtcg ccccttgtgt   16080 ggcactcttc tgcttcttta ttcagccagt atgtaacatc ccccatggt ctgaaatgat   16140 catctgttgg ccttggcctg tcgatgacac tcgaacggtg ttcggatccg agaaatgttt   16200
aaactaggcc tcctagcttg ggctgcaggt caatcccatt gcttttgaag cagctcaaca   16260
ttgatctctt tctcgaggtc attcatatgc ttgagaagag agtcgggata gtccaaaata   16320
aaacaaaggt aagattacct ggtcaaaagt gaaaacatca gttaaaaggt ggtataaagt   16380
aaaatatcgg taataaaagg tggcccaaag tgaaatttac tcttttctac tattataaaa   16440
attgaggatg ttttttgtcgg tactttgata cgtcattttt gtatgaattg gttttaagt   16500 ttattcgctt ttggaaatgc atatctgtat ttgagtcggg ttttaagttc gtttgctttt   16560
gtaaatacag agggatttgt ataagaaata tcttaaaaaa aacccatatg ctaatttgac   16620
```

-continued

```
ataattttg   agaaaaatat   atattcaggc   gaattctcac   aatgaacaat   aataagatta    16680
aaatagcttt   cccccgttgc   agcgcatggg   tattttttct   agtaaaaata   aaagataaac    16740
ttagactcaa   aacatttaca   aaaacaaccc   ctaaagttcc   taaagcccaa   agtgctatcc    16800
acgatccata   gcaagcccag   cccaacccaa   cccaacccaa   ccccacccag   tccagccaac    16860
tggacaatag   tctccacacc   cccccactat   caccgtgagt   tgtccgcacg   caccgcacgt    16920
ctcgcagcca   aaaaaaaaaa   aagaaagaaa   aaaagaaaa    agaaaaaaca   gcaggtgggt    16980
ccgggtcgtg   ggggccggaa   acgcgaggag   gatcgcgagc   cagcgacgag   gccggccctc    17040
cctccgcttc   caaagaaacg   cccccccatcg  ccactatata   catcccccc    cctctcctcc    17100
catcccccca   accctaccac   caccaccacc   accacctcca   cctcctcccc   cctcgctgcc    17160
ggacgacgcc   tcccccctcc   ccctccgccg   ccgccgcgcc   ggtaaccacc   ccgcccctct    17220
cctctttctt   tctccgtttt   ttttttccgt   ctcggtctcg   atctttggcc   ttggtagttt    17280
gggtgggcga   gaggcggctt   cgtgcgcgcc   cagatcggtg   cgcgggaggg   gcgggatctc    17340
gcggctgggg   ctctcgccgg   cgtggatccg   gcccggatct   cgcggggaat   ggggctctcg    17400
gatgtagatc   tgcgatccgc   cgttgttggg   ggagatgatg   gggggtttaa   aatttccgcc    17460
atgctaaaca   agatcaggaa   gaggggaaaa   gggcactatg   gtttatattt   ttatatattt    17520
ctgctgcttc   gtcaggctta   gatgtgctag   atctttcttt   cttcttttg    tgggtagaat    17580
ttgaatccct   cagcattgtt   catccggtagt  ttttcttttc   atgatttgtg   acaaatgcag    17640
cctcgtgcgg   agcttttttg   taggtagacc   atggctcatg   ctgccctcag   ccctctctcc    17700
caacgctttg   agagaatagc   tgtccagcca   ctcactggtg   tccttggtgc   tgagatcact    17760
ggagtggact   tgagggaacc   acttgatgac   agcacctgga   atgagatatt   ggatgccttc    17820
cacacttacc   aagtcatcta   ctttcctggc   caagcaatca   ccaatgagca   gcacattgca    17880
ttctcaagaa   ggtttggacc   agttgatcca   gtgcctcttc   tcaagagcat   tgaaggctat    17940
ccagaggttc   agatgatccg   cagagaagcc   aatgagtctg   gaaggtgat    tggtgatgac    18000
tggcacacag   actccacttt   ccttgatgca   cctccagctg   ctgttgtgat   gagggccata    18060
gatgttcctg   agcatggcgg   agacactggg   ttcctttcaa   tgtacacagc   ttgggagacc    18120
ttgtctccaa   ccatgcaagc   caccatcgaa   gggctcaacg   ttgtgcactc   tgccacacgt    18180
gtgttcggtt   ccctctacca   agcacagaac   cgtcgcttca   gcaacacctc   agtcaaggtg    18240
atggatgttg   atgctggtga   cagagagaca   gtccatccct   tggttgtgac   tcatcctggc    18300
tctggaagga   aaggccttta   tgtgaatcaa   gtctactgtc   agagaattga   gggcatgaca    18360
gatgcagaat   caaagccatt   gcttcagttc   ctctatgagc   atgccaccag   atttgacttc    18420
acttgccgtg   tgaggtggaa   gaaagaccaa   gtccttgtct   gggacaactt   gtgcaccatg    18480
caccgtgctg   ttcctgacta   tgctggcaag   ttcagatact   tgactcgcac   cacagttggt    18540
ggagttaggc   ctgcccgctg   agtagttagc   ttaatcacct   agagctcggt   cgcagcgtgt    18600
gcgtgtccgt   cgtacgttct   ggccggccgg   gccttgggcg   cgcgatcaga   agcgttcgt     18660
tggcgtgtgt   gtgcttctgg   tttgctttaa   ttttaccaag   tttgtttcaa   ggtggatcgc    18720
gtggtcaagg   cccgtgtgct   ttaaagaccc   accggcactg   gcagtgagtg   ttgctgcttg    18780
tgtaggcttt   ggtacgtatg   ggctttattt   gcttctggat   gttgtgtact   acttgggttt    18840
gttgaattat   tatgagcagt   tgcgtattgt   aattcagctg   ggctacctgg   acattgttat    18900
gtattaataa   atgctttgct   ttcttctaaa   gatctttaag   tgctgaattc   atatttcctc    18960
cttagtccgg   cagatggatc   acaggtacaa   tcctctacta   aacatcattt   gtctgataat    19020
```

```
cattggttgc ttgctctctg tcttctaca tgtttgcttg tacatgatct attttaaact   19080
tttgtcattc gcatgatcta tagttacttt tattgttgat caccgtaact tcttaatcat   19140
aaacaagagt gtgtcttctg tttcagggtt ctgcaacttc tgtccaagac caattgatgc   19200
cattgggtgt gataggaggg caaatgatgc cgtgggcacc tcgccagcca ggcatttggc   19260
caccgatgca aacacagatg ccaccgccga tgccgtgggg atttcctcct cgtgggcagt   19320
cacaatcacc aggattgccc tcacactcac caggatcagt acgttaagtt gatatccttt   19380
gcatctctat ttgcttcgtt gtttaagcag ttactagaaa acatgcatgt atatgttgca   19440
gtctatgtat atgtttaatt agttactcgg taaactaaca aatgtttgtt tcttttaaag   19500
ggttcaggct cacatcatgc tagtccgcct ccggatcaga gcacgtttat ggacttattg   19560
atgaacacaa gtggcggcgg ctccaatgac ccaccaacag aatgaattaa tatgaggct   19620 tgtgtggaac ttactatgat tgcgttttgt atggacttta acttgtttta gatggatttg   19680
aacttctttc gtatggactt gaacttgtat gaatattgaa tatggtgctt gtgttatgtt   19740
atgttgaata tggtgcttgt gttgtgatat attgaatgtt gtgcttatat tgtgctgtta   19800
tggaggcttc ccatccgggg agggagaaaa ataaaattgg atattaaaaa aaattattca   19860
ctaagagtgt cggcccccac actcttatat gcgcccaggt agcttactga tgtgcgcgca   19920
gtaagagtga cggccacggt actggccgac acttttaaca taagagtgtc ggttgcttgt   19980
tgaaccgaca ctttaacat aagagcgtcg gtccccacac ttctatacga ataagagcgt   20040 ccatttaga gtgacggcta agagtgtcgg tcaaccgaca ctcttatact tagagtgtcg   20100
gcttatttca gtaagagtgt ggggttttgg ccgacactcc ttacctttt tcttgtagtg   20160 acgagacacc tcaaggaccc atttaaatcg ttattagtaa ggcgcgtgat ggcgctctca   20220
gcttccccgg ctcaggaaga actgctgcag cctgctggga ggccgttgag gaagcagctt   20280
gctgcagccg cgaggagcat caactggagc tatgccctct tctggtccat ttcaagcact   20340
caacgacctc gggtgctgac gtggacggac gggttctaca atggcgaggt gaagacgcgt   20400
aagatctccc actccgtgga gctgacagcc gaccagctgc tcatgcagag gagcgagcag   20460
ctccgggagc tctacgaggc cctccggtcc ggcgagtgcg accgccgcgc ggcgcggccg   20520
gtgggctcgc tgtcgccgga ggacctcggg gacaccgagt ggtactacgt gatctgcatg   20580
acctacgcct tcctgccggg ccaaggcttg cccggcagga gttccgcgag caacgagcat   20640
gtctggctgt gcaacgcgca cctcgccggc agcaaggact ccccgcgcgc gctcctggcc   20700
aagagcgcgt ccattcagac aatcgtctgc atcccgctca tgggtggcgt gcttgagctt   20760
ggtactactg ataaggtgcc ggaggacccg gacttggtca gccgagcaac cgtagcattc   20820
tgggagccgc aatgtccgac atactcgaaa gagccgagct ccaacccgtc agcatacgaa   20880
accggggaag ccgcatacat agtcgtgttg gaggacctcg atcacaatgc catggacatg   20940
gagacggtga ctgccgccgc cgggagacac ggaaccggac aggagctagg agaagtcgag   21000
agcccgtcaa atgcaagcct ggagcacatc accaagggga tcgacgagtt ctacagcctc   21060
tgcgaggaaa tggacgtgca gccgctagag gatgcctgga taatggacgg gtctaatttc   21120
gaagtcccgt cgtcagcgct cccggtggat ggctcaagcg cacccgctga tggttctcgc   21180
gcgacaagtt tcgtggtttg gacgaggtca tcgcactcct gctcgggtga agcggcggcg   21240
gtgccggtca tcgaagagcc gcagaaattg ctgaagaaag cgttggccgg cggcggtgct   21300
tgggcgaaca cgaactgcgg tggcgggggc acgacggtaa cagcccagga aaacggcgcc   21360
aagaaccacg tcatgtcaga gcgaaagcgc cgggagaagc tcaacgagat gttcctcgtt   21420
```

```
ctcaagtcgt tggttccctc cattcacaag gtggacaaag catccatcct cgccgaaacg    21480
atagcctatc taaaggagct tcaacgaagg gtacaagaac tggaatccag gaggcaaggt    21540
ggcagtgggt gtgtcagcaa gaaagtctgt gtgggctcca actccaagag gaagagccca    21600
gagttcgccg gtggcgcgaa ggagcacccc tgggtcctcc ccatgacggg caccagcaac    21660
gtcaccgtca ccgtctcgga cacgaacgtg ctcctggagg tgcaatgccg gtgggagaag    21720
ctcctgatga cacgggtgtt cgacgccatc aagagcctcc atttggacgc tctctcggtt    21780
caggcttcgg caccagatgg cttcatgagg ctcaagatag gagctcagtt tgcaggctcc    21840
ggcgccgtcg tgcccggaat gatcagccaa tctcttcgta aagctatagg gaagcgatga    21900
aagggcgcta catgtgaagc ttaattaatg gaagcaaact tgtatttctt gtgcaaaagc    21960
ttactatata tttctgcaaa acctggtgtg ccttgttttg attttcagtc gccaattgtg    22020
cctttgtttt tatcaagtga tgatctacac tatatatatg gaatatttga aaaaaaaaaa    22080
aaaaaaaagg aattcatcga taagctggga gctcgaattt ccccgatcgt tcaaacattt    22140
ggcaataaag tttcttaaga ttgaatcctg ttgccggtct tgcgatgatt atcatataat    22200
ttctgttgaa ttacgttaag catgtaataa ttaacatgta atgcatgacg ttatttatga    22260
gatgggtttt tatgattaga gtcccgcaat tatacattta atacgcgata gaaaacaaaa    22320
tatagcgcgc aaactaggat aaattatcgc gcgcggtgtc atctatgtta ctagatcggg    22380
aattaagctt atataccgtc gacctcgagg ggggcccgg taccgtacag ttaaacttga    22440
attcagtaca ttaaaaacgt ccgcaatgtg ttattaagtt gtctaagcgt caatttgttt    22500
acaccacaat atatcctgcc a                                              22521

<210> SEQ ID NO 2
<211> LENGTH: 282
<212> TYPE: DNA
<213> ORGANISM: Sugarcane bacilliform virus

<400> SEQUENCE: 2
acaaagcatc gcataggatg cgcactcaca caccgaaagt tgagatgcct tctcagtgct     60
ttcatgggtc ctccacgctc catacgtcat tgcttacgat ctcctccact ggtcgtcatt    120
gcttacgtca gtgagatcga ctgcgtcttc tgcgccttcg acgttgtcgc cccttgtgtg    180
gcactcttct gcttctttat tcagccagta tgtaacatcc ccccatggtc tgaaatgatc    240
atctgttggc cttggcctgt cgatgacact cgaacggtgt tc                       282

<210> SEQ ID NO 3
<211> LENGTH: 6192
<212> TYPE: DNA
<213> ORGANISM: Artificial Sequence
<220> FEATURE:
<223> OTHER INFORMATION: oligonucleotide

<400> SEQUENCE: 3
cagtgtcact acaagaaaac gtcaaaggag tgtcagttaa ttaaagagtg tcggggccga     60
cactcttaat cgaagtaaaa gtgtgggttt tgctgcaccg acactcttaa tttaagagtg    120
tcggggtccc cgatgaaccg acgcttttaa tttaagagtg tgggttttc cacaccgaca    180 ctcttatgaa tgttacccta aattccccaa tcctattcta cagccgtcgt gcttcttctc    240
tcctttctcc ctgcccgccg tcagtatac agtcgaccgc caccgtctct ccagtctagc    300
cagcggcgtg cggcctcgcc gagccagcgt gggacgggcg gccagccac cagtggcggg    360 cgggctcgcc aagcagcgcc gggcgggcgg cctcgccaag cagagcgcgc acctccaagt    420
```

```
agcgccgggc ggccgagccg agccaggcgg cgggcggcct cgcagccaag ccagacgccg      480
ggcggcaggc ggcctcgggc gggcggcgtc gggcgggcgg cctcgccctg ccagcgggcg      540
acctcgcagc cgaggcagac gccgggcggg cagcctcact tagcgtaagc aaaatgtttc      600
tgcccaacct caggtccatg aattgtactc tcttcctgtg atgaaatgca agcacctgat      660
tacgagatga caacactgtc cagccaagac atgtttcatt gaaaatgatg gttagtacag      720
ggtttctgac tttctgttgt gcttgtttca ttgaaaataa tggtaaaagg tgcttgcatt      780
ctgtgcaaaa tcatgttcct gttgcccctg ttccagttct agaactcaag aagtcaaaac      840
gctatgtggt attaattgcc gacttaatgt ttttagtggc attgccactg atctagcatt      900
atgtcaagct taagaactct gttctcagcc tgagaaaagc cgttgctact gctgatttga      960 gagaggggg gggggagggg gcaaaaacta cagcaaaatg gtgggtgttt ttttcctgca     1020
ggcggccgct taattaaatt ttacacaaag catcgcatag gatgcgcact cacacaccga     1080
aagttgagat gccttctcag tgctttcatg ggtcctccac gctccatacg tcattgctta     1140
cgatctcctc cactggtcgt cattgcttac gtcagtgaga tcgactgcgt cttctgcgcc     1200
ttcgacgttg tcgcccttg tgtggcactc ttctgcttct ttattcagcc agtatgtaac     1260 atcccccat ggtctgaaat gatcatctgt tggccttggc ctgtcgatga cactcgaacg     1320
gtgttcggat ccgagtacac aaagcatcgc ataggatgcg cactcacaca ccgaaagttg     1380
agatgccttc tcagtgcttt catgggtcct ccacgctcca tacgtcattg cttacgatct     1440
cctccactgg tcgtcattgc ttacgtcagt gagatcgact gcgtcttctg cgccttcgac     1500
gttgtcgccc cttgtgtggc actcttctgc ttctttattc agccagtatg taacatcccc     1560
ccatggtctg aaatgatcat ctgttggcct tggcctgtcg atgacactcg aacggtgttc     1620
ggatccgagt acacaaagca tcgcatagga tgcgcactca cacaccgaaa gttgagatgc     1680
cttctcagtg ctttcatggg tcctccacgc tccatacgtc attgcttacg atctcctcca     1740
ctggtcgtca ttgcttacgt cagtgagatc gactgcgtct tctgcgcctt cgacgttgtc     1800
gccccttgtg tggcactctt ctgcttcttt attcagccag tatgtaacat cccccatgg     1860 tctgaaatga tcatctgttg gccttggcct gtcgatgaca ctcgaacggt gttcggatcc     1920
gagtacacaa agcatcgcat aggatgcgca ctcacacacc gaaagttgag atgccttctc     1980
agtgctttca tggtcctcc acgctccata cgtcattgct tacgatctcc tccactggtc     2040
gtcattgctt acgtcagtga gatcgactgc gtcttctgcg ccttcgacgt tgtcgcccct     2100
tgtgtggcac tcttctgctt ctttattcag ccagtatgta acatcccccc atggtctgaa     2160
atgatcatct gttggccttg gcctgtcgat gacactcgaa cggtgttcgg atccgagaaa     2220
tgtttaaact aggcctccta gcttgggctg caggtcaatc ccattgcttt tgaagcagct     2280
caacattgat ctctttctcg aggtcattca tatgcttgag aagagagtcg ggatagtcca     2340
aaataaaaca aaggtaagat tacctggtca aaagtgaaaa catcagttaa aaggtggtat     2400
aaagtaaaat atcggtaata aaaggtggcc caaagtgaaa tttactcttt tctactatta     2460
taaaaattga ggatgttttt gtcggtactt tgatacgtca tttttgtatg aattggtttt     2520
taagtttatt cgcttttgga aatgcatatc tgtatttgag tcgggtttta agttcgtttg     2580
cttttgtaaa tacagaggga tttgtataag aaatatcttt aaaaaaaccc atatgctaat     2640
ttgacataat ttttgagaaa aatatatatt caggcgaatt ctcacaatga acaataataa     2700
gattaaaata gctttccccc gttgcagcgc atgggtattt tttctagtaa aaataaaaga     2760
taaacttaga ctcaaaacat ttacaaaaac aaccccctaaa gttcctaaag cccaaagtgc     2820
```

| | |
|---|---|
| tatccacgat ccatagcaag cccagcccaa cccaacccaa cccaacccac cccagtccag | 2880 |
| ccaactggac aatagtctcc acacccccc actatcaccg tgagttgtcc gcacgcaccg | 2940 |
| cacgtctcgc agccaaaaaa aaaaaagaa agaaaaaaaa gaaaagaaa aaacagcagg | 3000 |
| tgggtccggg tcgtgggggc cggaaacgcg aggaggatcg cgagccagcg acgaggccgg | 3060 |
| ccctccctcc gcttccaaag aaacgccccc catcgccact atatacatac cccccctct | 3120 |
| cctcccatcc ccccaaccct accaccacca ccaccaccac ctccacctcc tccccctcg | 3180 |
| ctgccggacg acgcctcccc cctcccctc cgccgccgcc gcgccggtaa ccaccccgcc | 3240 |
| cctctcctct ttctttctcc gttttttttt tccgtctcgg tctcgatctt tggccttggt | 3300 |
| agtttgggtg ggcgagaggc ggcttcgtgc gcgcccagat cggtgcgcgg gagggcggg | 3360 |
| atctcgcggc tggggctctc gccggcgtgg atccggcccg gatctcgcgg ggaatggggc | 3420 |
| tctcggatgt agatctgcga tccgccgttg ttggggagga tgatgggggg tttaaaattt | 3480 |
| ccgccatgct aaacaagatc aggaagaggg gaaagggca ctatggttta tattttata | 3540 |
| tatttctgct gcttcgtcag gcttagatgt gctagatctt tctttcttct ttttgtgggt | 3600 |
| agaatttgaa tccctcagca ttgttcatcg gtagttttc ttttcatgat ttgtgacaaa | 3660 |
| tgcagcctcg tgcggagctt ttttgtaggt agaccatggc tcatgctgcc ctcagccctc | 3720 |
| tctcccaacg ctttgagaga atagctgtcc agccactcac tggtgtcctt ggtgctgaga | 3780 |
| tcactggagt ggacttgagg gaaccacttg atgcagcac ctggaatgag atattggatg | 3840 |
| ccttccacac ttaccaagtc atctactttc ctggccaagc aatcaccaat gagcagcaca | 3900 |
| ttgcattctc aagaaggttt ggaccagttg atccagtgcc tcttctcaag agcattgaag | 3960 |
| gctatccaga ggttcagatg atccgcagag aagccaatga gtctggaagg gtgattggtg | 4020 |
| atgactggca cacagactcc actttccttg atgcacctcc agctgctgtt gtgatgaggg | 4080 |
| ccatagatgt tcctgagcat ggcggagaca ctgggttcct ttcaatgtac acagctttggg | 4140 |
| agaccttgtc tccaaccatg caagccacca tcgaagggct caacgttgtg cactctgcca | 4200 |
| cacgtgtgtt cggttccctc taccaagcac agaaccgtcg cttcagcaac acctcagtca | 4260 |
| aggtgatgga tgttgatgct ggtgacagag agacagtcca tcccttggtt gtgactcatc | 4320 |
| ctggctctgg aaggaaaggc cttttatgtga atcaagtcta ctgtcagaga attgagggca | 4380 |
| tgacagatgc agaatcaaag ccattgcttc agttcctcta tgagcatgcc accagatttg | 4440 |
| acttcacttg ccgtgtgagg tggaagaaag accaagtcct tgtctgggac aacttgtgca | 4500 |
| ccatgcaccg tgctgttcct gactatgctg gcaagttcag atacttgact cgcaccacag | 4560 |
| ttggtggagt taggcctgcc cgctgagtag ttagcttaat cacctagagc tcggtcgcag | 4620 |
| cgtgtgcgtg tccgtcgtac gttctggccg gccgggcctt gggcgcgcga tcagaagcgt | 4680 |
| tgcgttggcg tgtgtgtgct tctggtttgc tttaattta ccaagtttgt ttcaaggtgg | 4740 |
| atcgcgtggt caaggcccgt gtgctttaaa gacccaccgg cactggcagt gagtgttgct | 4800 |
| gcttgtgtag gctttggtac gtatgggctt tatttgcttc tggatgttgt gtactacttg | 4860 |
| ggtttgttga attattatga gcagttgcgt attgtaattc agctgggcta cctggacatt | 4920 |
| gttatgtatt aataaatgct ttgctttctt ctaaagatct ttaagtgctg aattcatatt | 4980 |
| tcctcctagt ccggcagatg gatcacaggt acaatcctct actaaacatc atttgtctga | 5040 |
| taatcattgg ttgcttgctc tctgtctttc tacatgtttg cttgtacatg atctatttta | 5100 |
| aactttttgtc attcgcatga tctatagtta cttttattgt tgatcaccgt aacttcttaa | 5160 |
| tcataaacaa gagtgtgtct tctgtttcag ggttctgcaa cttctgtcca agaccaattg | 5220 |

-continued

| | |
|---|---|
| atgccattgg gtgtgatagg agggcaaatg atgccgtggg cacctcgcca gccaggcatt | 5280 |
| tggccaccga tgcaaacaca gatgccaccg ccgatgccgt ggggatttcc tcctcgtggg | 5340 |
| cagtcacaat caccaggatt gccctcacac tcaccaggat cagtacgtta agttgatatc | 5400 |
| ctttgcatct ctatttgctt cgttgtttaa gcagttacta gaaaacatgc atgtatatgt | 5460 |
| tgcagtctat gtatatgttt aattagttac tcggtaaact aacaaatgtt tgtttctttt | 5520 |
| aaagggttca ggctcacatc atgctagtcc gcctccggat cagagcacgt ttatggactt | 5580 |
| attgatgaac acaagtggcg gcggctccaa tgacccacca acagaatgaa ttaatatgga | 5640 |
| ggcttgtgtg gaacttacta tgattgcgtt ttgtatggac tttaacttgt tttagatgga | 5700 |
| tttgaacttc tttcgtatgg acttgaactt gtatgaatat tgaatatggt gcttgtgtta | 5760 |
| tgttatgttg aatatggtgc ttgtgttgtg atatattgaa tgttgtgctt atattgtgct | 5820 |
| gttatggagg cttcccatcc ggggagggag aaaaataaaa ttggatatta aaaaaaatta | 5880 |
| ttcactaaga gtgtcggccc ccacactctt atatgcgccc aggtagctta ctgatgtgcg | 5940 |
| cgcagtaaga gtgacggcca cggtactggc cgacactttt aacataagag tgtcggttgc | 6000 |
| ttgttgaacc gacactttta acataagagc gtcggtcccc acacttctat acgaataaga | 6060 |
| gcgtccattt tagagtgacg gctaagagtg tcggtcaacc gacactctta tacttagagt | 6120 |
| gtcggcttat ttcagtaaga gtgtggggtt ttggccgaca ctccttacct ttttttcttgt | 6180 |
| agtgacgaga ca | 6192 |

<210> SEQ ID NO 4
<211> LENGTH: 14
<212> TYPE: DNA
<213> ORGANISM: Artificial Sequence
<220> FEATURE:
<223> OTHER INFORMATION: oligonucleotide

<400> SEQUENCE: 4
cagtgtacga gaca                                                    14

<210> SEQ ID NO 5
<211> LENGTH: 13
<212> TYPE: DNA
<213> ORGANISM: Artificial Sequence
<220> FEATURE:
<223> OTHER INFORMATION: oligonucleotide

<400> SEQUENCE: 5
cagtgtcgag aca                                                     13

<210> SEQ ID NO 6
<211> LENGTH: 13
<212> TYPE: DNA
<213> ORGANISM: Artificial Sequence
<220> FEATURE:
<223> OTHER INFORMATION: oligonucleotide

<400> SEQUENCE: 6
cagtgtcgag acg                                                     13

<210> SEQ ID NO 7
<211> LENGTH: 13
<212> TYPE: DNA
<213> ORGANISM: Artificial Sequence
<220> FEATURE:
<223> OTHER INFORMATION: oligonucleotide

```
<400> SEQUENCE: 7
cagtgttgag aca                                                              13

<210> SEQ ID NO 8
<211> LENGTH: 13
<212> TYPE: DNA
<213> ORGANISM: Artificial Sequence
<220> FEATURE:
<223> OTHER INFORMATION: oligonucleotide

<400> SEQUENCE: 8
cagcgtcgag aca                                                              13

<210> SEQ ID NO 9
<211> LENGTH: 10
<212> TYPE: DNA
<213> ORGANISM: Artificial Sequence
<220> FEATURE:
<223> OTHER INFORMATION: oligonucleotide

<400> SEQUENCE: 9
cagtgagaca                                                                  10

<210> SEQ ID NO 10
<211> LENGTH: 22
<212> TYPE: DNA
<213> ORGANISM: Artificial Sequence
<220> FEATURE:
<223> OTHER INFORMATION: oligonucleotide

<400> SEQUENCE: 10
gtacctcttc ctggagcacc ag                                                    22

<210> SEQ ID NO 11
<211> LENGTH: 29
<212> TYPE: DNA
<213> ORGANISM: Artificial Sequence
<220> FEATURE:
<223> OTHER INFORMATION: oligonucleotide

<400> SEQUENCE: 11
tgtagaaccc gtccgtccgt ccacgtcag                                             29
```